US011912702B2

(12) United States Patent
Fuller et al.

(10) Patent No.: US 11,912,702 B2
(45) Date of Patent: *Feb. 27, 2024

(54) SUBSTITUTED PYRIDINES AS INHIBITORS OF HISTONE DEACETYLASE

(71) Applicant: Alkermes, Inc., Waltham, MA (US)

(72) Inventors: Nathan Oliver Fuller, Arlington, MA (US); John A. Lowe, III, Stonington, CT (US)

(73) Assignee: Alkermes, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/558,840

(22) Filed: Dec. 22, 2021

(65) Prior Publication Data

US 2022/0340558 A1 Oct. 27, 2022

Related U.S. Application Data

(63) Continuation of application No. 16/636,969, filed as application No. PCT/US2018/045528 on Aug. 7, 2018, now Pat. No. 11,225,475.

(60) Provisional application No. 62/541,807, filed on Aug. 7, 2017.

(51) Int. Cl.
*C07D 213/73* (2006.01)
*C07D 471/04* (2006.01)
*C07D 487/04* (2006.01)
*C07D 513/04* (2006.01)

(52) U.S. Cl.
CPC ......... *C07D 471/04* (2013.01); *C07D 487/04* (2013.01); *C07D 513/04* (2013.01)

(58) Field of Classification Search
CPC .................................................. C07D 213/73
USPC ....................................................... 546/308
See application file for complete search history.

(56) References Cited

U.S. PATENT DOCUMENTS

| | | |
|---|---|---|
| 5,112,824 A | 5/1992 | Baldwin et al. |
| 5,872,136 A | 2/1999 | Anthony et al. |
| 7,544,695 B2 | 6/2009 | Berk et al. |
| 7,834,026 B2 | 11/2010 | Berk et al. |
| 7,863,279 B2 | 1/2011 | Even et al. |
| 7,868,205 B2 | 1/2011 | Moradei et al. |
| 7,981,874 B2 | 7/2011 | Close et al. |
| 8,349,825 B2 | 1/2013 | Mampreian et al. |
| 8,461,189 B2 | 6/2013 | Heidebrecht, Jr. et al. |
| 8,686,020 B2 | 4/2014 | Hamblett et al. |
| 8,703,959 B2 | 4/2014 | Kutose et al. |
| 8,809,544 B2 | 8/2014 | Kutose et al. |
| 8,962,849 B2 | 2/2015 | Kutose et al. |
| 8,962,850 B2 | 2/2015 | Kutose et al. |
| 8,981,107 B2 | 3/2015 | Kutose et al. |
| 9,951,069 B1 | 4/2018 | Fuller et al. |
| 10,421,756 B2 | 9/2019 | Jefson et al. |
| 10,519,149 B2 | 12/2019 | Fuller et al. |
| 10,696,673 B2 | 6/2020 | Fuller et al. |
| 10,793,567 B2 | 10/2020 | Fuller et al. |
| 10,919,902 B2 | 2/2021 | Jefson et al. |
| 11,225,475 B2 | 1/2022 | Fuller et al. |
| 11,225,479 B2 | 1/2022 | Fuller et al. |
| 11,286,256 B2 | 3/2022 | Fuller et al. |
| 2002/0183324 A1 | 12/2002 | Jacobson et al. |
| 2003/0187026 A1 | 10/2003 | Li et al. |
| 2003/0199511 A1 | 10/2003 | Li et al. |
| 2005/0025995 A1 | 2/2005 | Cheng et al. |
| 2005/0153981 A1 | 7/2005 | Li et al. |
| 2005/0245530 A1 | 11/2005 | Borzilleri et al. |
| 2006/0173050 A1 | 8/2006 | Liu et al. |
| 2006/0235028 A1 | 10/2006 | Li et al. |
| 2006/0270686 A1 | 11/2006 | Kelly et al. |
| 2007/0004741 A1 | 1/2007 | Apodaca et al. |
| 2007/0037794 A1 | 2/2007 | Ungashe et al. |
| 2007/0135437 A1 | 6/2007 | Benjamin et al. |
| 2008/0064871 A1 | 3/2008 | Hirata et al. |
| 2008/0103182 A1 | 5/2008 | Ackermann et al. |
| 2008/0132503 A1 | 6/2008 | Moradei et al. |
| 2008/0280891 A1 | 11/2008 | Kelly et al. |
| 2009/0022047 A1 | 1/2009 | Seto et al. |
| 2009/0058982 A1 | 3/2009 | Seto et al. |
| 2009/0062297 A1 | 3/2009 | Heidebrecht et al. |
| 2009/0156825 A1 | 6/2009 | Heidebrecht, Jr. et al. |
| 2009/0207712 A1 | 8/2009 | Seto et al. |
| 2009/0286782 A1 | 11/2009 | Ibrahim et al. |
| 2009/0286783 A1 | 11/2009 | Ibrahim et al. |
| 2009/0306086 A1 | 12/2009 | Ibrahim et al. |
| 2009/0306087 A1 | 12/2009 | Ibrahim et al. |
| 2010/0041670 A1 | 2/2010 | Even et al. |
| 2010/0099676 A1 | 4/2010 | Endoh et al. |
| 2010/0310500 A1 | 12/2010 | Graupe et al. |

(Continued)

FOREIGN PATENT DOCUMENTS

| | | |
|---|---|---|
| CN | 101808518 A | 8/2010 |
| CN | 103601718 A | 2/2014 |

(Continued)

OTHER PUBLICATIONS

Abel et al., pigenetic targets of HDAC inhibition in neurodegenerative and psychiatric disorders. Curr Opin Pharmacol. Feb. 2008;8(1):57-64.

Bennett et al., Cecil Textbook of Medicine, 2th Edition, W.B. Sanders Company, Philadelphia. vol. 1, pp. 1004-1010, (1996).

(Continued)

*Primary Examiner* — Douglas M Willis

(74) *Attorney, Agent, or Firm* — McCarter & English, LLP; Michael J. DeGrazia

(57) ABSTRACT

Provided herein are compounds and pharmaceutically acceptable salts thereof, and pharmaceutical compositions thereof, which are useful in the treatment of conditions associated with inhibition of HDAC (e.g,. HDAC2).

10 Claims, No Drawings

(56) References Cited

U.S. PATENT DOCUMENTS

| | | | |
|---|---|---|---|
| 2011/0009365 A1 | 1/2011 | Dubois et al. |
| 2011/0021494 A1 | 1/2011 | Maier et al. |
| 2011/0105472 A1 | 5/2011 | Greul et al. |
| 2011/0118248 A1 | 5/2011 | Ungashe et al. |
| 2011/0224155 A1 | 9/2011 | Tachdjian et al. |
| 2012/0184572 A1 | 7/2012 | Song et al. |
| 2012/0295881 A1 | 11/2012 | Lange et al. |
| 2013/0210880 A1 | 8/2013 | Amberg et al. |
| 2013/0331382 A1 | 12/2013 | Hubbard et al. |
| 2014/0128391 A1 | 5/2014 | van Duzer et al. |
| 2014/0187780 A1 | 7/2014 | Kim et al. |
| 2014/0329684 A1 | 11/2014 | Muller et al. |
| 2014/0364605 A1 | 12/2014 | Li et al. |
| 2015/0057300 A1 | 2/2015 | Tafesse et al. |
| 2015/0094329 A1 | 4/2015 | Nokura et al. |
| 2015/0266866 A1 | 9/2015 | Conn et al. |
| 2015/0322076 A1 | 11/2015 | Chen et al. |
| 2016/0096833 A1 | 4/2016 | Emmitte et al. |
| 2016/0347761 A1 | 12/2016 | Holson et al. |
| 2018/0009818 A1 | 1/2018 | Miyazaki et al. |
| 2018/0194769 A1 | 7/2018 | Jefson et al. |
| 2021/0276977 A1 | 9/2021 | Fuller et al. |
| 2021/0276978 A1 | 9/2021 | Fuller et al. |
| 2021/0277007 A1 | 9/2021 | Jefson et al. |
| 2022/0340560 A1 | 10/2022 | Fuller et al. |

FOREIGN PATENT DOCUMENTS

| | | |
|---|---|---|
| CN | 103864754 A | 6/2014 |
| CN | 105777632 A | 7/2016 |
| CN | 106946890 A | 7/2017 |
| DE | 4212748 A1 | 10/1993 |
| EP | 2712655 A1 | 4/2014 |
| GB | 2515785 A | 1/2015 |
| GB | 2516303 A | 1/2015 |
| JP | H11-049676 A | 2/1999 |
| JP | H11-209366 A | 8/1999 |
| JP | 2003-192673 A | 7/2003 |
| JP | 2003-300940 A | 10/2003 |
| JP | 2008-094847 A | 4/2008 |
| JP | 2008-179067 A | 8/2008 |
| JP | 2008-179068 A | 8/2008 |
| JP | 2009-023986 A | 2/2009 |
| JP | 2009-514858 A | 4/2009 |
| JP | 2009-516743 A | 4/2009 |
| JP | 2009-523725 A | 6/2009 |
| JP | 2009-209090 A | 9/2009 |
| JP | 2009-536615 A | 10/2009 |
| JP | 2010-524908 A | 7/2010 |
| JP | 2010-531358 A | 9/2010 |
| JP | 2010-539206 A | 12/2010 |
| JP | 2012-107001 A | 6/2012 |
| JP | 2012-529435 A | 11/2012 |
| JP | 2013-020223 A | 1/2013 |
| JP | 5-208961 B2 | 6/2013 |
| JP | 2014-101353 A | 6/2014 |
| JP | 2014-523857 A | 9/2014 |
| JP | 2014-523857 A | 9/2014 |
| TW | 201808286 A | 3/2018 |
| TW | 201825473 A | 7/2018 |
| WO | WO-1992/01675 A2 | 2/1992 |
| WO | WO-1996/11929 A1 | 4/1996 |
| WO | WO-1996/11930 A1 | 4/1996 |
| WO | WO-1996/18617 A1 | 6/1996 |
| WO | WO-1996/21660 A1 | 7/1996 |
| WO | WO-1996/23783 A1 | 8/1996 |
| WO | WO-1996/32938 A1 | 10/1996 |
| WO | WO-1997/08167 A1 | 3/1997 |
| WO | WO-1997/15557 A1 | 5/1997 |
| WO | WO-1997/36901 A1 | 10/1997 |
| WO | WO-1998/55472 A1 | 12/1998 |
| WO | WO-1999/65897 A1 | 12/1999 |
| WO | WO-2000/002860 A1 | 1/2000 |
| WO | WO-2000/055114 A1 | 9/2000 |
| WO | WO-2001/021597 A1 | 3/2001 |
| WO | WO-2002/014315 A2 | 2/2002 |
| WO | WO-2002/020011 A2 | 3/2002 |
| WO | WO-2002/026708 A1 | 4/2002 |
| WO | WO-2002/032900 A2 | 4/2002 |
| WO | WO-2002/046172 A2 | 6/2002 |
| WO | WO-2002/053160 A1 | 7/2002 |
| WO | WO-2002/068417 A2 | 9/2002 |
| WO | WO-2002/089738 A2 | 11/2002 |
| WO | WO-2003/042190 A1 | 5/2003 |
| WO | WO-2003/051366 A2 | 6/2003 |
| WO | WO-2003/055447 A2 | 7/2003 |
| WO | WO-2003/059269 A2 | 7/2003 |
| WO | WO-2003/062224 A1 | 7/2003 |
| WO | WO-2003/095437 A1 | 11/2003 |
| WO | WO-2004/000318 A2 | 12/2003 |
| WO | WO-2004/000820 A2 | 12/2003 |
| WO | WO-2004/016597 A2 | 2/2004 |
| WO | WO-2004/045518 A2 | 6/2004 |
| WO | WO-2004/071426 A2 | 8/2004 |
| WO | WO-2004/072033 A2 | 8/2004 |
| WO | WO-2005/009988 A1 | 2/2005 |
| WO | WO-2005/014580 A1 | 2/2005 |
| WO | WO-2005/016862 A1 | 2/2005 |
| WO | 2005/030705 A1 | 4/2005 |
| WO | WO-2005/079802 A1 | 9/2005 |
| WO | WO-2005/095386 A1 | 10/2005 |
| WO | WO-2005/097740 A1 | 10/2005 |
| WO | WO-2005/121093 A1 | 12/2005 |
| WO | WO-2006/019833 A1 | 2/2006 |
| WO | WO-2006/044975 A2 | 4/2006 |
| WO | WO-2006/051311 A1 | 5/2006 |
| WO | WO-2006/065479 A2 | 6/2006 |
| WO | WO-2006/067445 A2 | 6/2006 |
| WO | WO-2006/067446 A1 | 6/2006 |
| WO | WO-2006/076644 A2 | 7/2006 |
| WO | WO-2006/077168 A1 | 7/2006 |
| WO | WO-2006/080884 A1 | 8/2006 |
| WO | WO-2006/084017 A2 | 8/2006 |
| WO | WO-2006/120133 A2 | 11/2006 |
| WO | WO-2006/128129 A2 | 11/2006 |
| WO | WO-2006/128172 A2 | 11/2006 |
| WO | WO-2006/130403 A1 | 12/2006 |
| WO | WO-2006/135604 A2 | 12/2006 |
| WO | WO-2006/137772 A1 | 12/2006 |
| WO | WO-2007/002313 A2 | 1/2007 |
| WO | WO-2007/008541 A2 | 1/2007 |
| WO | WO-2007/049158 A2 | 5/2007 |
| WO | WO-2007/050980 A2 | 5/2007 |
| WO | WO-2007/055374 A1 | 5/2007 |
| WO | WO-2007/055941 A2 | 5/2007 |
| WO | WO-2007/056341 A1 | 5/2007 |
| WO | WO-2007/061880 A1 | 5/2007 |
| WO | WO-2007/061978 A1 | 5/2007 |
| WO | WO-2007/064797 A2 | 6/2007 |
| WO | WO-2007/071598 A1 | 6/2007 |
| WO | WO-2007/087129 A2 | 8/2007 |
| WO | WO-2007/087130 A2 | 8/2007 |
| WO | WO-2007/118137 A1 | 10/2007 |
| WO | WO-2007/119463 A1 | 10/2007 |
| WO | WO-2007/122830 A1 | 11/2007 |
| WO | WO-2007/125984 A1 | 11/2007 |
| WO | WO-2007/126765 A1 | 11/2007 |
| WO | WO-2007/129044 A1 | 11/2007 |
| WO | WO-2007/129052 A1 | 11/2007 |
| WO | WO-2007/138072 A2 | 12/2007 |
| WO | WO-2007/139002 A1 | 12/2007 |
| WO | WO-2007/143557 A2 | 12/2007 |
| WO | WO-2008/005457 A2 | 1/2008 |
| WO | WO-2008/009963 A2 | 1/2008 |
| WO | WO-2008/010985 A2 | 1/2008 |
| WO | WO-2008/011611 A2 | 1/2008 |
| WO | WO-2008/012418 A1 | 1/2008 |
| WO | WO-2008/013963 A2 | 1/2008 |
| WO | WO-2008/016643 A2 | 2/2008 |
| WO | WO-2008/024970 A2 | 2/2008 |
| WO | WO-2008/024978 A2 | 2/2008 |
| WO | WO-2008/036272 A1 | 3/2008 |
| WO | WO-2008/047229 A2 | 4/2008 |
| WO | WO-2008/053913 A1 | 5/2008 |

(56) References Cited

FOREIGN PATENT DOCUMENTS

| | | |
|---|---|---|
| WO | WO-2008/067874 A1 | 6/2008 |
| WO | WO-2008/074788 A1 | 6/2008 |
| WO | WO-2008/078837 A1 | 7/2008 |
| WO | WO-2008/092199 A1 | 8/2008 |
| WO | WO-2008/093024 A2 | 8/2008 |
| WO | WO-2008/115262 A2 | 9/2008 |
| WO | WO-2008/115719 A1 | 9/2008 |
| WO | WO-2008/119015 A2 | 10/2008 |
| WO | WO-2008/129280 A1 | 10/2008 |
| WO | WO-2008/139152 A1 | 11/2008 |
| WO | WO-2008/145843 A1 | 12/2008 |
| WO | WO-2008/151184 A1 | 12/2008 |
| WO | WO-2008/151211 A1 | 12/2008 |
| WO | WO-2008/154221 A2 | 12/2008 |
| WO | WO-2009/005638 A2 | 1/2009 |
| WO | WO-2009/022171 A1 | 2/2009 |
| WO | WO-2009/032861 A1 | 3/2009 |
| WO | WO-2009/037001 A2 | 3/2009 |
| WO | WO-2009/052319 A1 | 4/2009 |
| WO | WO-2009/078992 A1 | 6/2009 |
| WO | WO-2009/100406 A2 | 8/2009 |
| WO | WO-2009/109710 A1 | 9/2009 |
| WO | WO-2009/115267 A2 | 9/2009 |
| WO | WO-2009/156484 A2 | 12/2009 |
| WO | WO-2010/006191 A1 | 1/2010 |
| WO | WO-2010/007046 A2 | 1/2010 |
| WO | WO-2010/007756 A1 | 1/2010 |
| WO | WO-2010/008739 A2 | 1/2010 |
| WO | WO-2010/032147 A2 | 3/2010 |
| WO | WO-2010/034838 A2 | 4/2010 |
| WO | WO-2010/046780 A2 | 4/2010 |
| WO | WO-2010/068863 A2 | 6/2010 |
| WO | WO-2010/075376 A2 | 7/2010 |
| WO | WO-2010/088574 A1 | 8/2010 |
| WO | WO-2010/108921 A1 | 9/2010 |
| WO | WO-2010/111527 A1 | 9/2010 |
| WO | WO-2010/112520 A1 | 10/2010 |
| WO | WO-2010/127855 A1 | 11/2010 |
| WO | WO-2010/137350 A1 | 12/2010 |
| WO | WO-2010/151747 A1 | 12/2010 |
| WO | WO-2011/008931 A2 | 1/2011 |
| WO | WO-2011/012661 A1 | 2/2011 |
| WO | WO-2011/072275 A2 | 6/2011 |
| WO | WO-2011/073328 A1 | 6/2011 |
| WO | WO-2011/082400 A2 | 7/2011 |
| WO | WO-2011/119869 A1 | 9/2011 |
| WO | WO-2011/125568 A1 | 10/2011 |
| WO | WO-2011/133920 A1 | 10/2011 |
| WO | WO-2011/134925 A1 | 11/2011 |
| WO | WO-2012/003405 A1 | 1/2012 |
| WO | WO-2012/004217 A1 | 1/2012 |
| WO | WO-2012/020131 A2 | 2/2012 |
| WO | WO-2012/020133 A1 | 2/2012 |
| WO | WO-2012/024604 A2 | 2/2012 |
| WO | WO-2012/061337 A1 | 5/2012 |
| WO | WO-2012/064559 A1 | 5/2012 |
| WO | WO-2012/074050 A1 | 6/2012 |
| WO | WO-2012/085650 A1 | 6/2012 |
| WO | WO-2012/085789 A1 | 6/2012 |
| WO | WO-2012/101062 A1 | 8/2012 |
| WO | WO-2012/117097 A1 | 9/2012 |
| WO | WO-2012/123745 A1 | 9/2012 |
| WO | WO-2012/127385 A1 | 9/2012 |
| WO | WO-2012/147890 A1 | 11/2012 |
| WO | WO-2012/149540 A1 | 11/2012 |
| WO | WO-2012/152915 A1 | 11/2012 |
| WO | WO-2012/154880 A1 | 11/2012 |
| WO | WO-2012/156918 A1 | 11/2012 |
| WO | WO-2012/156919 A1 | 11/2012 |
| WO | WO-2012/156920 A1 | 11/2012 |
| WO | WO-2012/166951 A1 | 12/2012 |
| WO | WO-2013/013815 A1 | 1/2013 |
| WO | WO-2013/013817 A1 | 1/2013 |
| WO | WO-2013/017480 A1 | 2/2013 |
| WO | WO-2013/024004 A1 | 2/2013 |
| WO | WO-2013/033068 A1 | 3/2013 |
| WO | WO-2013/038390 A1 | 3/2013 |
| WO | WO-2013/041602 A1 | 3/2013 |
| WO | WO-2013/055984 A1 | 4/2013 |
| WO | WO-2013/059648 A1 | 4/2013 |
| WO | WO-2013/064884 A1 | 5/2013 |
| WO | WO-2013/152198 A1 | 10/2013 |
| WO | WO-2013/152727 A1 | 10/2013 |
| WO | WO-2013/163404 A1 | 10/2013 |
| WO | WO-2013/178816 A1 | 12/2013 |
| WO | WO-2013/180193 A1 | 12/2013 |
| WO | WO-2013/188813 A2 | 12/2013 |
| WO | WO-2014/000418 A1 | 1/2014 |
| WO | WO-2014/005125 A2 | 1/2014 |
| WO | WO-2014/012511 A1 | 1/2014 |
| WO | WO-2014/015167 A2 | 1/2014 |
| WO | WO-2014/025808 A1 | 2/2014 |
| WO | WO-2014/031928 A2 | 2/2014 |
| WO | WO-2014/047111 A1 | 3/2014 |
| WO | WO-2014/055955 A1 | 4/2014 |
| WO | WO-2014/056620 A1 | 4/2014 |
| WO | WO-2014/074906 A1 | 5/2014 |
| WO | WO-2014/081299 A1 | 5/2014 |
| WO | WO-2014/081300 A1 | 5/2014 |
| WO | WO-2014/081301 A1 | 5/2014 |
| WO | WO-2014/081303 A1 | 5/2014 |
| WO | WO-2014/089112 A1 | 6/2014 |
| WO | WO-2014/144169 A1 | 9/2014 |
| WO | WO-2014/146995 A1 | 9/2014 |
| WO | WO-2014/149164 A1 | 9/2014 |
| WO | WO-2014/151936 A1 | 9/2014 |
| WO | WO-2014/153208 A1 | 9/2014 |
| WO | WO-2014/164704 A2 | 10/2014 |
| WO | WO-2014/181287 A1 | 11/2014 |
| WO | WO-2014/187297 A1 | 11/2014 |
| WO | WO-2014/187298 A1 | 11/2014 |
| WO | WO-2014/190199 A1 | 11/2014 |
| WO | WO-2014/194270 A1 | 12/2014 |
| WO | WO-2015/031725 A1 | 3/2015 |
| WO | WO-2015/035059 A1 | 3/2015 |
| WO | WO-2015/051043 A1 | 4/2015 |
| WO | WO-2015/051458 A1 | 4/2015 |
| WO | WO-2015/061247 A2 | 4/2015 |
| WO | WO-2015/077246 A1 | 5/2015 |
| WO | WO-2015/110999 A1 | 7/2015 |
| WO | WO-2015/120800 A1 | 8/2015 |
| WO | WO-2015/140572 A1 | 9/2015 |
| WO | WO-2015/142903 A2 | 9/2015 |
| WO | WO-2015/157057 A1 | 10/2015 |
| WO | WO-2015/170218 A1 | 11/2015 |
| WO | 2016/018795 A1 | 2/2016 |
| WO | WO-2016/020307 A1 | 2/2016 |
| WO | WO-2016/042341 A1 | 3/2016 |
| WO | WO-2016/057779 A2 | 4/2016 |
| WO | WO-2016/058544 A1 | 4/2016 |
| WO | WO-2016/061527 A1 | 4/2016 |
| WO | WO-2016/100711 A1 | 6/2016 |
| WO | WO-2016/133838 A1 | 8/2016 |
| WO | WO-2016/173557 A1 | 11/2016 |
| WO | WO-2016/176657 A1 | 11/2016 |
| WO | WO-2016/183266 A1 | 11/2016 |
| WO | WO-2017/007755 A1 | 1/2017 |
| WO | WO-2017/007756 A1 | 1/2017 |
| WO | WO-2017/027984 A1 | 2/2017 |
| WO | WO-2017/044889 A1 | 3/2017 |
| WO | WO-2017/046133 A1 | 3/2017 |
| WO | WO-2017/075694 A1 | 5/2017 |
| WO | WO-2017/106818 A1 | 6/2017 |
| WO | WO-2017/146116 A1 | 8/2017 |
| WO | WO-2017/156265 A1 | 9/2017 |
| WO | WO-2018/132531 A1 | 7/2018 |

OTHER PUBLICATIONS

Bowers et al., The Class I HDAC inhibitor RGFP963 enhances consolidation of cued fear extinction. Learn Mem. Mar. 16, 2015;22(4):225-31.

CAS Registry No. 1072874-82-8. Entered STN: Nov. 14, 2008, 1 page.

(56) References Cited

OTHER PUBLICATIONS

CDC, CDC and Fungal Diseases. Retrieved online at: http://www.cdc.gov/ncezid/dfwed/mycotics. 2 pages, Sep. 2011.

Choong et al., A novel histone deacetylase 1 and 2 isoform-specific inhibitor alleviates experimental Parkinson's Disease. Neurobiology of Aging. DOI: 10.1016/j.neurobiolaging.2015.10.001, 54 pages, Oct. 2, 2015.

Dorostkar et al., Analyzing dendritic spine pathology in Alzheimer's disease: problems and opportunities. Acta Neuropathol. Jul. 2015;130(1):1-19.

Faraco et al., The therapeutic potential of HDAC inhibitors in the treatment of multiple sclerosis. Mol Med. May-Jun. 2011;17(5-6):442-7.

Fischer et al., Recovery of learning and memory is associated with chromatin remodelling. Nature. May 10, 2007;447(7141):178-82.

Graff et al., An epigenetic blockade of cognitive functions in the neurodegenerating brain. Nature. Feb. 29, 2012;483(7388):222-6.

Grohol, Symptoms & Treatments of Mental Disorders. Mental Disorders & Conditions—DSM. Retrieved online at: https://psychcentral.com/disorders/ 9 pages, Feb. 27, 2019.

Guan et al., HDAC2 negatively regulates memory formation and synaptic plasticity. Nature. May 7, 2009;459(7243):55-60.

Gura, Systems for identifying new drugs are often faulty. Science. Nov. 7, 1997;278(5340):1041-2.

Herman et al., Histone deacetylase inhibitors reverse gene silencing in Friedreich's ataxia. Nat Chem Biol. Oct. 2006;2(10):551-8.

Johnson et al., Relationships between drug activity in NCI preclinical in vitro and in vivo models and early clinical trials. Br J Cancer. May 18, 2001;84(10):1424-31.

Kattar et al., Parallel medicinal chemistry approaches to selective HDAC1/HDAC2 inhibitor (SHI-1:2) optimization. Bioorg Med Chem Lett. Feb. 15, 2009;19(4):1168-72.

Levenson et al., Regulation of histone acetylation during memory formation in the hippocampus. J Biol Chem. Sep. 24, 2004;279(39):40545-59.

Masliah et al., Altered expression of synaptic proteins occurs early during progression of Alzheimer's disease. Neurology. Jan. 9, 2001;56(1):127-9.

MedicineNet.com, Definition of Cancer. Retrieved online at: http://www.medterms.com. 1 page, Sep. 18, 2004.

Medlineplus, Infections. Retrieved online at: https://medlineplus.gov/infections.html. 10 pages, Jul. 6, 2016.

Methot et al., Exploration of the internal cavity of histone deacetylase (HDAC) with selective HDAC1/HDAC2 inhibitors (SHI-1:2). Bioorg Med Chem Lett. Feb. 1, 2008;18(3):973-8.

Mielcarek et al., SAHA decreases HDAC 2 and 4 levels in vivo and improves molecular phenotypes in the R6/2 mouse model of Huntington's disease. PLoS One. 2011;6(11):e27746, 10 pages.

Pearce et al., Failure modes in anticancer drug discovery and development. Cancer Drug Design and Discovery. Elsevier Inc., Stephen Neidle (Ed.). Chapter 18, pp. 424-435, (2008).

Qin et al., Social deficits in Shank3-deficient mouse models of autism are rescued by histone deacetylase (HDAC) inhibition. Nat Neurosci. Apr. 2018;21(4):564-575.

Schulz-Schaeffer, The synaptic pathology of alpha-synuclein aggregation in dementia with Lewy bodies, Parkinson's disease and Parkinson's disease dementia. Acta Neuropathol. Aug. 2010;120(2):131-43.

She et al., Selectivity and Kinetic Requirements of HDAC Inhibitors as Progranulin Enhancers for Treating Frontotemporal Dementia. Cell Chem Biol. Jul. 20, 2017;24(7):892-906.e5.

Sprow et al., Histone acetylation in the nucleus accumbens shell modulates ethanol-induced locomotor activity in DBA/2J mice. Alcohol Clin Exp Res. Sep. 2014;38(9):2377-86.

Stevens, Fungal Skin Infections. UNM School of Medicine, Continuum of Care. Retrieved online at: hsc.unm.edu/som/coc. 1 page, (2000).

Tan et al., Upregulation of histone deacetylase 2 in laser capture nigral microglia in Parkinson's disease. Neurobiol Aging. Aug. 2018; 8 pages, pre-publication version.

UCSF Medical Center, Neurological Disorders. Retrieved online at: https://www.ucshealth.org/conditions/neurological_disorders/ 1 page, (2016).

University of Maryland Medical Center, Myeloproliferative disorders. Retrieved online at: http://www.umm.edu/health/medical/altmed/condition/myeloproliferative-disorders. 8 pages, (2017).

Wagner et al., Kinetically Selective Inhibitors of Histone Deacetylase 2 (HDAC2) as Cognition Enhancers. Chem Sci. Jan. 1, 2015;6(1):804-815.

Xu et al., Dendritic spine dysgenesis in Rett syndrome. Front Neuroanat. Sep. 10, 2014;8:97. 8 pages.

Zhu et al., Investigation on the isoform selectivity of histone deacetylase inhibitors using chemical feature based pharmacophore and docking approaches. Eur J Med Chem. May 2010;45(5):1777-91.

U.S. Appl. No. 17/674,165, filed Feb. 17, 2022, Pending.

U.S. Appl. No. 17/559,488, filed Dec. 22, 2021, Pending.

Ho et al., Thirty Years of HDAC Inhibitors: 2020 Insight and Hindsight. J Med Chem. Nov. 12, 2020;63(21):12460-12484.

Patani et al., Bioisosterism: A Rational Approach in Drug Design. Chem Rev. Dec. 19, 1996;96(8):3147-3176.

Wermuth et al., Molecular Variations Based on Isosteric Replacements. The Practice of Medicinal Chemistry. Academic Press Limited. Chapter 13, pp. 203-237, (1996).

U.S. Appl. No. 15/741,609, filed Jan. 3, 2018, U.S. Pat. No. 10,421,756, Issued.

U.S. Appl. No. 15/741,657, filed Jan. 3, 2018, 2018-0194769, Abandoned.

U.S. Appl. No. 16/726,990, filed Dec. 26, 2019, U.S. Pat. No. 10,919,902, Issued.

U.S. Appl. No. 17/134,875, filed Dec. 28, 2020, 2021-0277007, Published.

U.S. Appl. No. 15/867,982, filed Jan. 11, 2018, U.S. Pat. No. 9,951,069, Issued.

U.S. Appl. No. 15/934,299, filed Mar. 23, 2018, U.S. Pat. No. 10,519,149, Issued.

U.S. Appl. No. 16/681,213, filed Nov. 12, 2019, U.S. Pat. No. 10,696,673, Issued.

U.S. Appl. No. 16/880,075, filed May 21, 2020, U.S. Pat. No. 11,286,256, Issued.

U.S. Appl. No. 17/674,165, filed Feb. 17, 2022, Abandoned.

U.S. Appl. No. 17/950,571, filed Sep. 22, 2022, Abandoned.

U.S. Appl. No. 18/199,251, filed May 18, 2023, Pending.

U.S. Appl. No. 16/636,969, filed Feb. 6, 2020, U.S. Pat. No. 11,225,475, Issued.

U.S. Appl. No. 17/260,192, filed Jan. 13, 2021, 2021-0276977, Published.

U.S. Appl. No. 17/260,193, filed Jan. 13, 2021, 2021-0276978, Published.

U.S. Appl. No. 16/477,466, filed Jul. 11, 2019, U.S. Pat. No. 10,793,567, Issued.

U.S. Appl. No. 17/007,151, filed Aug. 31, 2020, U.S. Pat. No. 11,225,479, Issued.

U.S. Appl. No. 17/559,488, filed Dec. 22, 2021, 2022-0340560, Published.

SUBSTITUTED PYRIDINES AS INHIBITORS OF HISTONE DEACETYLASE

RELATED APPLICATIONS

This application is a 35 U.S.C. § 371 national stage filing of International Application No. PCT/US2018/045528, filed Aug. 7, 2018, which in turn claims priority to U.S. Provisional Application No. 62/541,807, filed Aug. 7, 2017. The entire contents of each of the foregoing applications are incorporated herein by reference.

STATEMENT REGARDING FEDERALLY SPONSORED RESEARCH AND DEVELOPMENT

This invention was made with government support under Small Business Innovation Research (SBIR) grant 1R43AG048651-01A1 awarded by the National Institute of Health (NIH). The government has certain rights in the invention.

BACKGROUND OF THE INVENTION

Inhibitors of histone deacetylases (HDAC) have been shown to modulate transcription and to induce cell growth arrest, differentiation and apoptosis. HDAC inhibitors also enhance the cytotoxic effects of therapeutic agents used in cancer treatment, including radiation and chemotherapeutic drugs. Marks, P., Rifkind, R. A., Richon, V. M., Breslow, R., Miller, T., Kelly, W. K. Histone deacetylases and cancer: causes and therapies. Nat Rev Cancer, 1, 194-202, (2001); and Marks, P. A., Richon, V. M., Miller, T., Kelly, W. K. Histone deacetylase inhibitors. Adv Cancer Res, 91, 137-168, (2004). Moreover, recent evidence indicates that transcriptional dysregulation may contribute to the molecular pathogenesis of certain neurodegenerative disorders, such as Huntington's disease, spinal muscular atrophy, amyotropic lateral sclerosis, and ischemia. Langley, B., Gensert, J. M., Beal, M. F., Ratan, R. R. Remodeling chromatin and stress resistance in the central nervous system: histone deacetylase inhibitors as novel and broadly effective neuroprotective agents. Curr Drug Targets CNS Neurol Disord, 4, 41-50, (2005). A recent review has summarized the evidence that aberrant histone acetyltransferase (HAT) and histone deacetylases (HDAC) activity may represent a common underlying mechanism contributing to neurodegeneration. Moreover, using a mouse model of depression, Nestler has recently highlighted the therapeutic potential of histone deacetylation inhibitors (HDAC5) in depression. Tsankova, N. M., Berton, O., Renthal, W., Kumar, A., Neve, R. L., Nestler, E. J. Sustained hippocampal chromatin regulation in a mouse model of depression and antidepressant action. Nat Neurosci, 9, 519-525, (2006).

There are 18 known human histone deacetylases, grouped into four classes based on the structure of their accessory domains. Class I includes HDAC1, HDAC2, HDAC3, and HDAC8 and has homology to yeast RPD3. HDAC4, HDAC5, HDAC7, and HDAC9 belong to class IIa and have homology to yeast. HDAC6 and HDAC10 contain two catalytic sites and are classified as class IIb. Class III (the sirtuins) includes SIRT1, SIRT2, SIRT3, SIRT4, SIRT5, SIRT6, and SIRT7. HDAC11 is another recently identified member of the HDAC family and has conserved residues in its catalytic center that are shared by both class I and class II deacetylases and is sometimes placed in class IV.

In contrast, HDACs have been shown to be powerful negative regulators of long-term memory processes. Non-specific HDAC inhibitors enhance synaptic plasticity as well as long-term memory (Levenson et al., 2004, J. Biol. Chem. 279:40545-40559; Lattal et al., 2007, Behav Neurosci 121: 1125-1131; Vecsey et al., 2007, J. Neurosci 27:6128; Bredy, 2008, Learn Mem 15:460-467; Guan et al., 2009, Nature 459:55-60; Malvaez et al., 2010, Biol. Psychiatry 67:36-43; Roozendaal et al., 2010, J. Neurosci. 30:5037-5046). For example, HDAC inhibition can transform a learning event that does not lead to long-term memory into a learning event that does result in significant long-term memory (Stefanko et al., 2009, Proc. Natl. Acad. Sci. USA 106:9447-9452). Furthermore, HDAC inhibition can also generate a form of long-term memory that persists beyond the point at which normal memory fails. HDAC inhibitors have been shown to ameliorate cognitive deficits in genetic models of Alzheimer's disease (Fischer et al., 2007, Nature 447:178-182; Kilgore et al., 2010, Neuropsychopharmacology 35:870-880). These demonstrations suggest that modulating memory via HDAC inhibition has considerable therapeutic potential for many memory and cognitive disorders.

Currently, the role of individual HDACs in long-term memory has been explored in two recent studies. Kilgore et al. 2010, Neuropsychopharmacology 35:870-880 revealed that nonspecific HDAC inhibitors, such as sodium butyrate, inhibit class I HDACs (HDAC1, HDAC2, HDAC3, HDAC8) with little effect on the class IIa HDAC family members (HDAC4, HDAC5, HDAC7, HDAC9). This suggests that inhibition of class I HDACs may be critical for the enhancement of cognition observed in many studies. Indeed, forebrain and neuron specific over expression of HDAC2, but not HDAC1, decreased dendritic spine density, synaptic density, synaptic plasticity and memory formation (Guan et al., 2009, Nature, 459:55-60). In contrast, HDAC2 knockout mice exhibited increased synaptic density, increased synaptic plasticity and increased dendritic density in neurons. These HDAC2 deficient mice also exhibited enhanced learning and memory in a battery of learning behavioral paradigms. This work demonstrates that HDAC2 is a key regulator of synaptogenesis and synaptic plasticity. Additionally, Guan et al. showed that chronic treatment of mice with SAHA (an HDAC 1, 2, 3, 6, 8 inhibitor) reproduced the effects seen in the HDAC2 deficient mice and recused the cognitive impairment in the HDAC2 overexpression mice.

The inhibition of the HDAC2 (selectively or in combination with inhibition of other class I HDACs) is an attractive therapeutic target. Such inhibition has the potential for enhancing cognition and facilitating the learning process through increasing synaptic and dendritic density in neuronal cell populations. In addition, inhibition of HDAC2 may also be therapeutically useful in treating a wide variety of other diseases and disorders.

BRIEF SUMMARY OF THE INVENTION

Disclosed are compounds and pharmaceutically acceptable salts thereof, and pharmaceutical compositions, which are useful in the treatment of conditions associated with the activity of HDAC (e.g., HDAC2). See e.g., Table 1.

One of the advantages of certain compounds described herein is that they possess enhanced safety parameters. For example, the inclusion of an additional fluorine atom on the bottom phenyl ring of certain compounds provided almost a 2-fold increase in safety, showing fewer effects on human erythroid and myeloid progenitors. See e.g., Table 4, Comparator 1 vs Compound 10; Comparator 2 vs. Compound 3;

Comparator 5 vs. Compound 1; and Comparator 6 vs. Compound 2. A similar result was seen between regioisomers (compare Comparator 4 with Compound 8) and the replacement of hydrogen for fluorine (compare Comparator 3 with Compound 6).

Conditions which are treatable by the disclosed compounds include, but are not limited to, neurological disorders, memory or cognitive function disorders or impairments, extinction learning disorders, fungal diseases or infections, inflammatory diseases, hematological diseases, neoplastic diseases, psychiatric disorders, and memory loss.

DETAILED DESCRIPTION OF THE INVENTION

1. Compounds

Provided herein are compounds having the formula selected from:

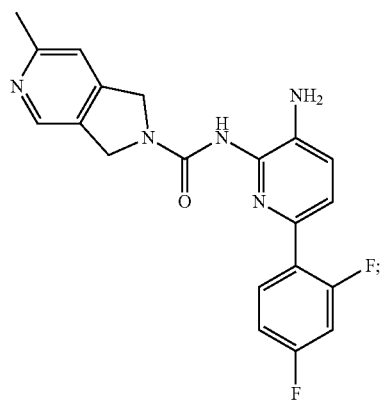

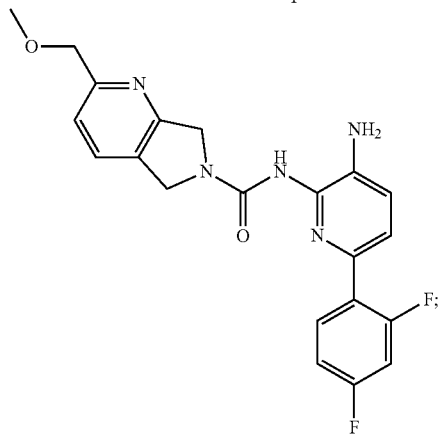

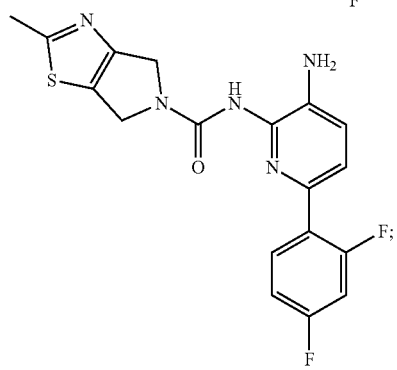

-continued

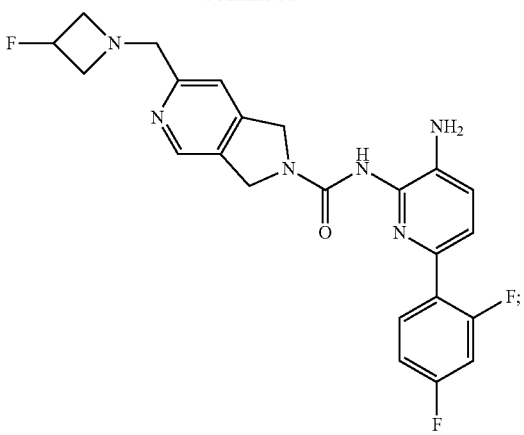

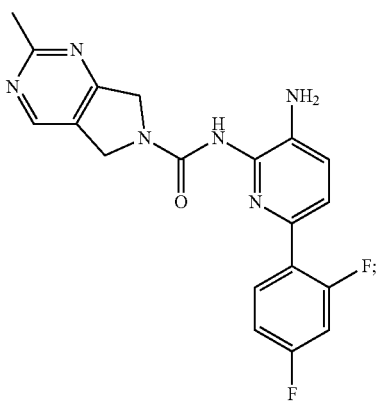

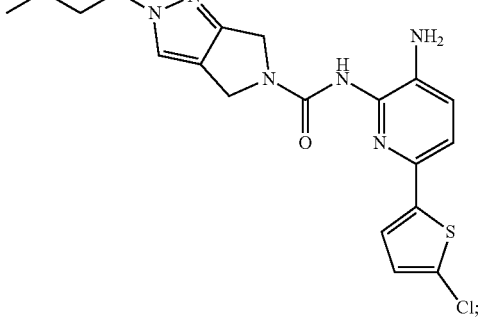

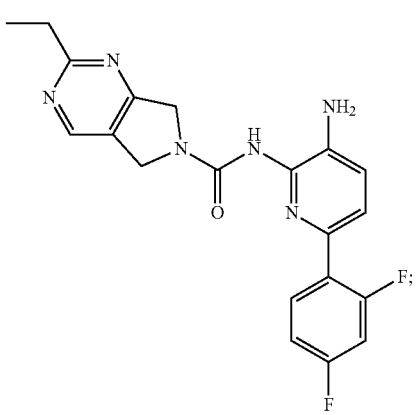

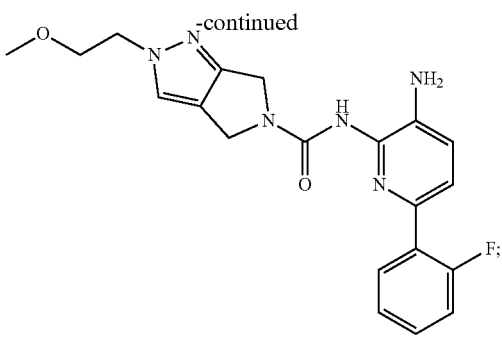

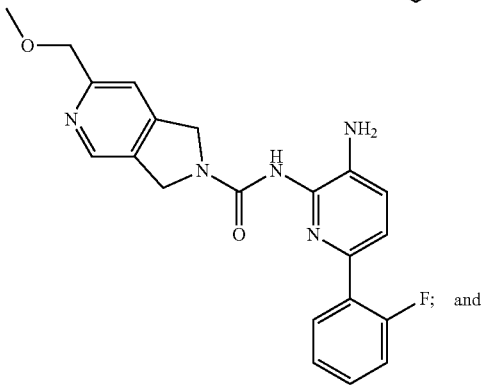

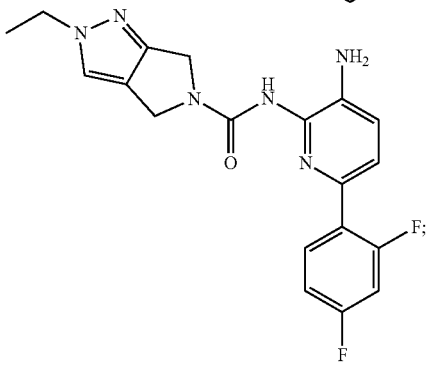

or a pharmaceutically acceptable salt thereof.

Other examples of compounds included in the present disclosure are provided in the EXEMPLIFICATION section. Pharmaceutically acceptable salts as well as the neutral forms of these compounds are included.

2. Definitions

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Pharmaceutically acceptable salts as well as the neutral forms of the compounds described herein are included. For use in medicines, the salts of the compounds refer to non-toxic "pharmaceutically acceptable salts." Pharmaceutically acceptable salt forms include pharmaceutically acceptable acidic/anionic or basic/cationic salts. Pharmaceutically acceptable basic/cationic salts include, the sodium, potassium, calcium, magnesium, diethanolamine, n-methyl-D-glucamine, L-lysine, L-arginine, ammonium, etha- nolamine, piperazine and triethanolamine salts. Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The term "effective amount" or "therapeutically effective amount" includes an amount of a compound described herein that will elicit a biological or medical response of a subject e.g., between 0.01-100 mg/kg body weight/day of the provided compound, such as e.g., 0.1-100 mg/kg body weight/day.

3. Uses, Formulation and Administration

In some embodiments, compounds and compositions described herein are useful in treating conditions associated with the activity of HDAC. Such conditions include for example, those described below.

Recent reports have detailed the importance of histone acetylation in central nervous system ("CNS") functions such as neuronal differentiation, memory formation, drug addiction, and depression (Citrome, Psychopharmacol. Bull. 2003, 37, Suppl. 2, 74-88; Johannessen, CNS Drug Rev. 2003, 9, 199-216; Tsankova et al., 2006, Nat. Neurosci. 9, 519-525). Thus, in one aspect, the provided compounds and compositions may be useful in treating a neurological disorder. Examples of neurological disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, muscular dystrophy, olivopontocerebellar atrophy, multiple system atrophy, Wilson's disease, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, restless leg syndrome, vertigo as result of CNS degeneration; pathologies arising with chronic alcohol or drug abuse including, for example, the degeneration of neurons in locus coeruleus and cerebellum, drug-induced movement disorders; pathologies arising with aging including degeneration of cerebellar neurons and cortical neurons leading to cognitive and motor impairments; and pathologies arising with chronic amphetamine abuse to including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurological disorders affecting sensory neurons include Friedreich's ataxia, diabetes, peripheral neuropathy, and retinal neuronal degeneration. Other neurological disorders include nerve injury or trauma associated with spinal cord injury. Neurological disorders of limbic and cortical systems include cerebral amyloidosis, Pick's atrophy, and Retts syndrome. In another aspect, neurological disorders include disorders of mood, such as affective disorders and anxiety; disorders of social behavior, such as character defects and personality disorders; disorders of learning, memory, and intelligence, such as mental retardation and dementia. Thus, in one aspect the disclosed compounds and compositions may be useful in treating schizophrenia, delirium, attention deficit disorder (ADD), schizoaffective disorder, Alzheimer's disease, Rubinstein-Taybi syndrome, depression, mania, attention deficit disorders, drug addiction, dementia, agitation, apathy, anxiety, psychoses, personality disorders, bipolar disorders, unipolar affective disorder, obsessive-compulsive disorders, eating disorders, post-traumatic stress disorders, irritability, adolescent conduct disorder and disinhibition.

Transcription is thought to be a key step for long-term memory processes (Alberini, 2009, Physiol. Rev. 89, 121-145). Transcription is promoted by specific chromatin modifications, such as histone acetylation, which modulate histone-DNA interactions (Kouzarides, 2007, Cell, 128:693-705). Modifying enzymes, such as histone acetyltransferases (HATs) and histone deacetylases (HDACs), regulate the state of acetylation on histone tails. In general, histone acetylation promotes gene expression, whereas histone deacetylation leads to gene silencing. Numerous studies have shown that a potent HAT, cAMP response element-binding protein (CREB)-binding protein (CBP), is necessary for long-lasting forms of synaptic plasticity and long term memory (for review, see Barrett, 2008, Learn Mem 15:460-467). Thus, in one aspect, the provided compounds and compositions may be useful for promoting cognitive function and enhancing learning and memory formation.

The compounds and compositions described herein may also be used for treating fungal diseases or infections.

In another aspect, the compounds and compositions described herein may be used for treating inflammatory diseases such as stroke, rheumatoid arthritis, lupus erythematosus, ulcerative colitis and traumatic brain injuries (Leoni et al., PNAS, 99(5); 2995-3000(2002); Suuronen et al. J. Neurochem. 87; 407-416 (2003) and Drug Discovery Today, 10: 197-204 (2005).

In yet another aspect, the compounds and compositions described herein may be used for treating a cancer caused by the proliferation of neoplastic cells. Such cancers include e.g., solid tumors, neoplasms, carcinomas, sarcomas, leukemias, lymphomas and the like. In one aspect, cancers that may be treated by the compounds and compositions described herein include, but are not limited to: cardiac cancer, lung cancer, gastrointestinal cancer, genitourinary tract cancer, liver cancer, nervous system cancer, gynecological cancer, hematologic cancer, skin cancer, and adrenal gland cancer. In one aspect, the compounds and compositions described herein are useful in treating cardiac cancers selected from sarcoma (angiosarcoma, fibrosarcoma, rhabdomyosarcoma, liposarcoma), myxoma, rhabdomyoma, fibroma, lipoma and teratoma. In another aspect, the compounds and compositions described herein are useful in treating a lung cancer selected from bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, and mesothelioma. In one aspect, the compounds and compositions described herein are useful in treating a gastrointestinal cancer selected from esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), and large bowel (adenocarcinoma, tubular adenoma, villous adenoma, hamartoma, leiomyoma). In one aspect, the compounds and compositions described herein are useful in treating a genitourinary tract cancer selected from kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). In one aspect, the compounds and compositions described herein are useful in treating a liver cancer selected from hepatoma (hepatocellular carcinoma), cholangiocarcinoma, hepatoblastoma, angiosarcoma, hepatocellular adenoma, and hemangioma.

In some embodiments, the compounds described herein relate to treating, a bone cancer selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochondroma (osteocartilaginous exostoses), benign chondroma, chondroblastoma, chondromyxofibroma, osteoid osteoma and giant cell tumors.

In one aspect, the compounds and compositions described herein are useful in treating a nervous system cancer selected from skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), and spinal cord (neurofibroma, meningioma, glioma, sarcoma).

In one aspect, the compounds and compositions described herein are useful in treating a gynecological cancer selected from uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

In one aspect, the compounds and compositions described herein are useful in treating a skin cancer selected from malignant melanoma, basal cell carcinoma, squamous cell carcinoma, Karposi's sarcoma, moles dysplastic nevi, lipoma, angioma, dermatofibroma, keloids, and psoriasis.

In one aspect, the compounds and compositions described herein are useful in treating an adrenal gland cancer selected from neuroblastoma.

In one aspect, the compounds and compositions described herein are useful in treating cancers that include, but are not limited to: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In one aspect, the present disclosure provides a method of treating a condition described herein comprising administering to a subject an effective amount of a compound, or pharmaceutically acceptable salt described herein, or a composition thereof.

Also provided is one or more of the compounds, or pharmaceutically acceptable salts thereof described herein, or a provided composition, for treating a condition described herein.

Also provided is the use of one or more of the compounds, or pharmaceutically acceptable salts thereof described herein for the manufacture of a medicament for treating a condition described herein.

Subjects may also be selected to be suffering from one or more of the described conditions before treatment with one or more of the described compounds, or pharmaceutically acceptable salts or compositions commences.

The present disclosure also provides pharmaceutically acceptable compositions comprising a compound described herein, or a pharmaceutically acceptable salt thereof; and a pharmaceutically acceptable carrier. These compositions can be used to treat one or more of the conditions described above.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of a compound are included herein.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

EXEMPLIFICATION

General Information

Spots were visualized by UV light (254 and 365 nm). Purification by column and flash chromatography was carried out using silica gel (200-300 mesh). Solvent systems are reported as the ratio of solvents.

$^1$H NMR spectra were recorded on Bruker Avance III 400 MHz or a Bruker Fourier 300 MHz. $^1$H chemical shifts are reported in δ values in ppm with tetramethylsilane (TMS, =0.00 ppm) as the internal standard. See, e.g., the data provided in Table 1.

LCMS spectra were obtained on an Agilent 1200 series 6110 or 6120 mass spectrometer with ESI (+) ionization mode. (Column: C18 (50×4.6 mm, 5 m) operating in ES (+) or (−) ionization mode; T=30° C.; flow rate=1.5 mL/min; detected wavelength: 220 nm. See, e.g., the data provided in Table 1.

Example 1. Synthesis of Compound 1

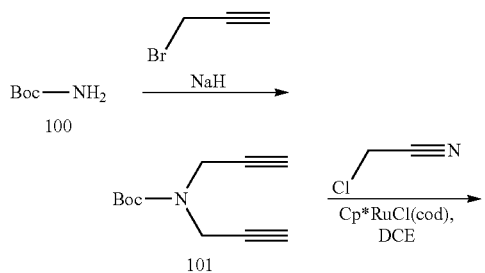

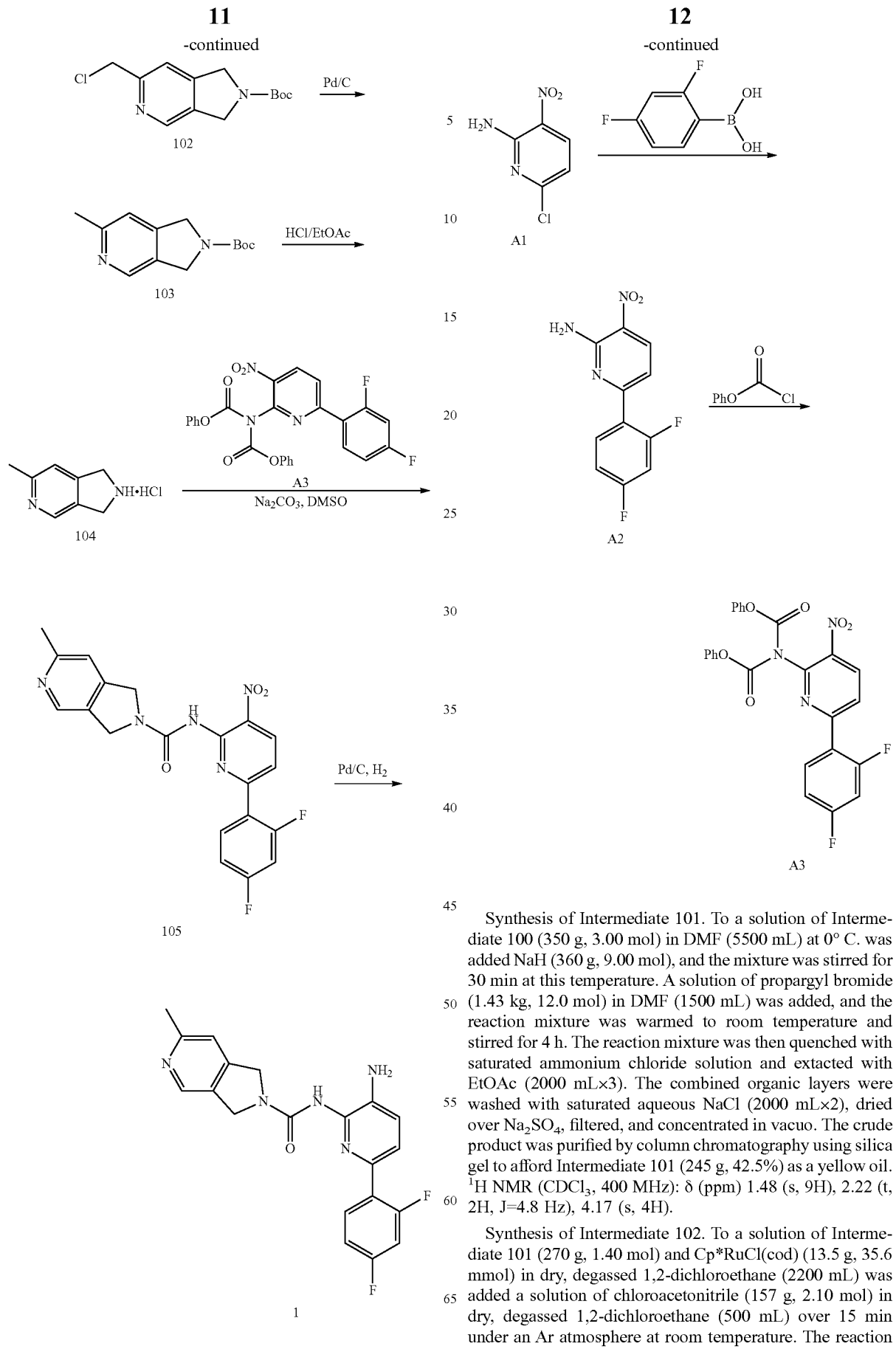

Synthesis of Intermediate 101. To a solution of Intermediate 100 (350 g, 3.00 mol) in DMF (5500 mL) at 0° C. was added NaH (360 g, 9.00 mol), and the mixture was stirred for 30 min at this temperature. A solution of propargyl bromide (1.43 kg, 12.0 mol) in DMF (1500 mL) was added, and the reaction mixture was warmed to room temperature and stirred for 4 h. The reaction mixture was then quenched with saturated ammonium chloride solution and extacted with EtOAc (2000 mL×3). The combined organic layers were washed with saturated aqueous NaCl (2000 mL×2), dried over $Na_2SO_4$, filtered, and concentrated in vacuo. The crude product was purified by column chromatography using silica gel to afford Intermediate 101 (245 g, 42.5%) as a yellow oil. $^1$H NMR ($CDCl_3$, 400 MHz): δ (ppm) 1.48 (s, 9H), 2.22 (t, 2H, J=4.8 Hz), 4.17 (s, 4H).

Synthesis of Intermediate 102. To a solution of Intermediate 101 (270 g, 1.40 mol) and Cp*RuCl(cod) (13.5 g, 35.6 mmol) in dry, degassed 1,2-dichloroethane (2200 mL) was added a solution of chloroacetonitrile (157 g, 2.10 mol) in dry, degassed 1,2-dichloroethane (500 mL) over 15 min under an Ar atmosphere at room temperature. The reaction mixture was then warmed to 60° C. and stirred for 0.5 h, whereupon the solvent was evaporated and the crude residue was purified by column chromatography using silica gel to give Intermediate 102 (210 g, 56.0%) as an off-white solid. $^1$H NMR (CDCl$_3$, 400 MHz): δ (ppm) 1.52 (s, 9H), 4.67-4.73 (m, 6H), 7.40 (d, 1H, J=19.2 Hz), 8.50 (d, 1H, J=15.6 Hz). MS 269.1 [M+H]$^+$.

Synthesis of Intermediate 103. A solution of Intermediate 102 (210 g, 784 mmol) in MeOH (4000 mL) was treated with Pd/C (21.0 g), and the reaction mixture was stirred at room temperature under an H$_2$ atmosphere for 2 h. The reaction mixture was then filtered, and the filtrate was concentrated in vacuo to provide Intermediate 103 (120 g, 65.6%) as an off-white solid. $^1$H NMR (CDCl$_3$, 400 MHz): δ (ppm) 1.53 (s, 9H), 2.98 (s, 3H), 4.86-4.90 (m, 4H), 7.53-7.60 (m, 1H), 8.62-8.67 (m, 1H). MS 235.1 [M+H]$^+$.

Synthesis of Intermediate 104. A solution of 4N HCl (600 mL, HCl in EtOAc) was added dropwise to a 0° C. solution of Intermediate 103 (120 g, 513 mmol) in EtOAc (600 mL). The reaction mixture was then warmed to room temperature and stirred for 1 h. The solvent was removed by filtration to give Intermediate 104 as a white solid. $^1$H NMR (DMSO_d$_6$, 400 MHz): δ (ppm) 2.75 (s, 3H), 4.73-4.80 (m, 4H), 7.97 (s, 1H), 8.20 (s, 1H). MS 135.1 [M+H]$^+$.

Synthesis of Intermediate 105. A mixture of Intermediate 104 (513 mmol), Intermediate A3 (151 g, 308 mmol) and Na$_2$CO$_3$ (272 g, 2.57 mol) in DMSO was stirred at room temperature for 3 h. After the reaction had reached completion according to LCMS, the reaction mixture was poured into cold water, extracted with EtOAc, and the layers were separated. The organic layer was then concentrated in vacuo, and the residue was triturated with EtOAc, and then filtered to provide Intermediate 105 (80.0 g, 38% from compound 5) as a yellow solid. $^1$H NMR (DMSO_d$_6$, 400 MHz): δ (ppm) 2.49 (s, 3H), 4.70-4.96 (m, 4H), 7.29-7.35 (m, 2H), 7.45-7.49 (m, 1H), 7.50-7.51 (m, 1H), 8.08-8.14 (m, 1H), 8.46 (d, 2H, J=8.4 Hz), 10.11 (brs, 1H). MS 412.1 [M+H]$^+$.

Synthesis of Compound 1. A mixture of Intermediate 105 (80.0 g, 195 mmol) and Pd/C (8.00 g) in MeOH (2500 mL) was stirred at room temperature for 1 h under a H$_2$ atmosphere. After 1 h, Pd/C was removed by filtration through Celite. The filtrate was concentrated and the residue was purified by silica gel column chromatography to provide Compound 1 (52.0 g, 70.3%) as a gray solid. $^1$H NMR (DMSO_d$_6$, 400 MHz): δ (ppm) 2.48 (s, 3H), 4.77 (s, 4H), 5.28 (s, 2H), 7.16-7.18 (m, 2H), 7.28-7.31 (m, 2H), 7.40-7.42 (m, 1H), 7.92-7.94 (m, 1H), 8.45 (s, 1H), 8.56 (s, 1H). MS 382.1 [M+H]$^+$.

Synthesis of Intermediate A2. A mixture of Intermediate A1 (300 g, 1.73 mol), 4-fluorophenylboronic acid (265 g, 1.91 mmol) and Cs$_2$CO$_3$ (1.13 kg, 3.46 mol) in dioxane/H$_2$O (6000 mL/600 mL) was treated with Pd(PPh$_3$)$_4$(72.6 g, 86.3 mmol) under a N$_2$ atmosphere. The mixture was stirred at 95° C. for 2 h and then was concentrated in vacuo. The residue was taken up in EtOAc (4000 mL) and the resulting solution was washed with brine (1000 mL×3). The combined organic layers were dried over anhydrous Na$_2$SO$_4$, filtered, and then concentrated in vacuo. The crude residue was purified by column chromatography on silica gel to provide Intermediate A2 (240 g, crude) as a yellow solid. $^1$H NMR (CDCl$_3$, 400 MHz): δ (ppm) 6.90-6.96 (m, 1H), 6.99-7.04 (m, 1H), 7.23-7.26 (m, 1H), 8.02-8.08 (m, 1H), 8.47 (d, 1H, J=8.4 Hz). MS 252.0 [M+H]$^+$.

Synthesis of Intermediate A3. Phenyl carbonochloridate (354 g, 2.27 mol) was added dropwise to a stirring solution of Intermediate A2 (240 g, crude) in pyridine (4800 mL) at room temperature. After the addition was completed, the reaction mixture was heated to 50° C. and stirred overnight. The mixture was then concentrated in vacuo, and the crude residue was purified by recrystallization with MTBE to provide Intermediate A3 (240 g, 28.2% from compound A1) as a yellow solid. $^1$H NMR (CDCl$_3$, 400 MHz): δ (ppm) 6.97-7.02 (m, 1H), 7.08-7.39 (m, 11H), 8.13 (d, 1H, J=8.4 Hz), 8.24-8.30 (m, 1H), 8.67 (d, 1H, J=8.8 Hz). MS 492.1 [M+H]$^+$.

Example 2. Synthesis of Compound 2

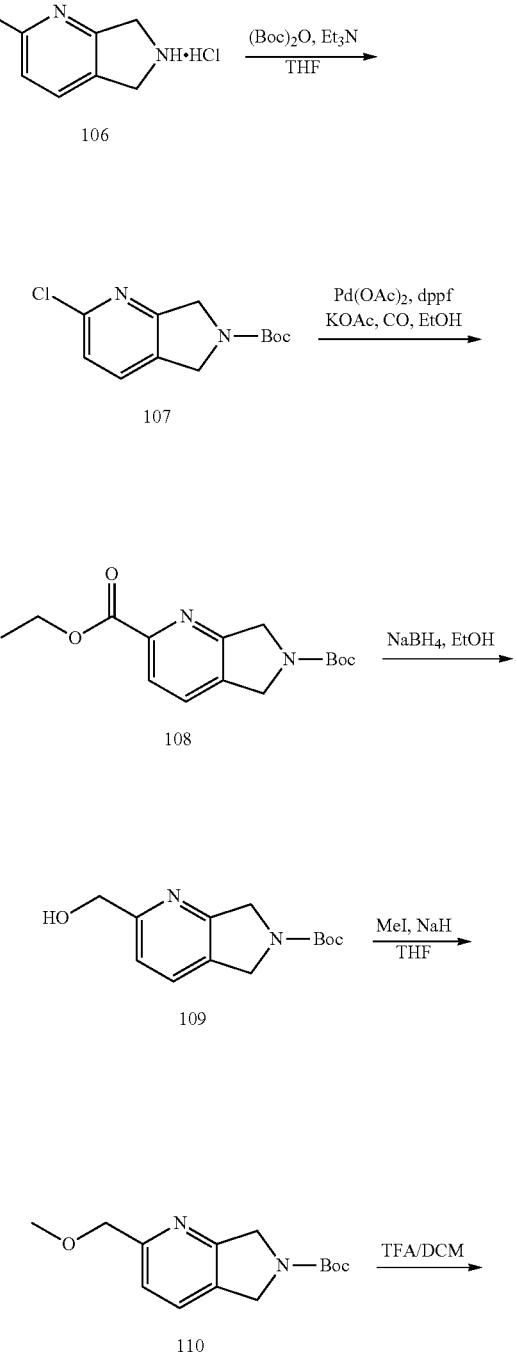

-continued

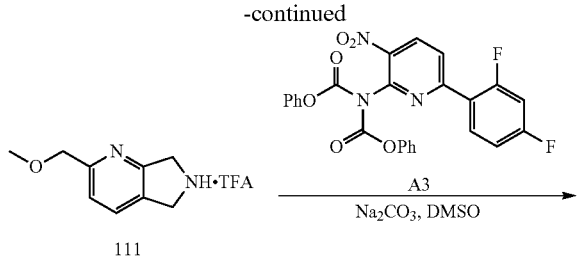

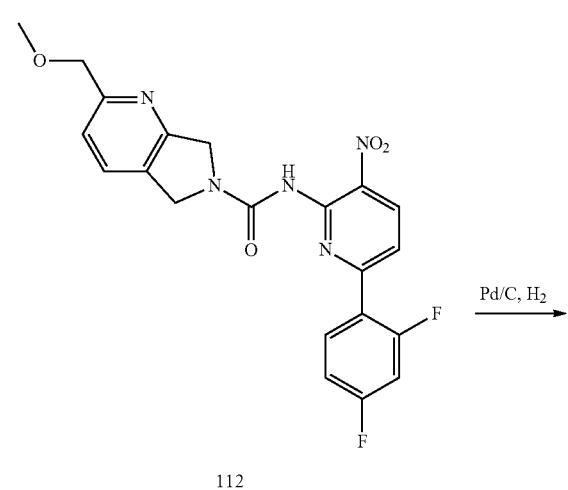

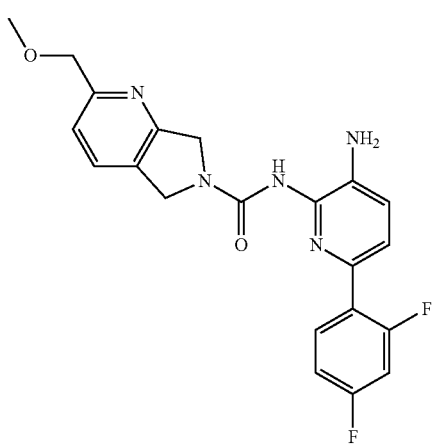

Synthesis of 107. A mixture of 2-chloro-6,7-dihydro-5H-pyrrolo[3,4-b]pyridine hydrochloride (11 g, 57.9 mmol), TEA (17.5 g, 173.7 mmol) and (Boc)$_2$O (13.9 g, 63.7 mmol) in THF (250 mL) was stirred at room temperature for 3 h. The reaction mixture was then poured into DCM (500 mL), washed with brine (100 mL×3), dried over anhydrous Na$_2$SO$_4$ and then concentrated in vacuo. The residue was purified by column chromatography on silica gel (DCM:EtOAc=100:1~10:1) to give 107 (13.5 g, 92%) as a white solid. MS 255.2 [M+H]$^+$.

Synthesis of 108. A mixture of 107 (13.5 g, 53.1 mmol), potassium acetate (10.4 g, 106.2 mmol), dppf (883 mg, 1.59 mmol) and palladium acetate (677 mg, 2.66 mmol) in ethanol (20 mL) was stirred at 100° C. for 16 h under a CO atmosphere at 1.5 MPa. The reaction mixture was then cooled to room temperature and filtered through Celite. The filtrate was concentrated in vacuo and the residue was dissolved in DCM (500 mL), washed with brine (10 mL×3), dried over anhydrous Na$_2$SO$_4$ and then concentrated in vacuo. The residue was purified by column chromatography on silica gel (PE:EtOAc=8:1~3:1) to give 108 (13.4 g, 86%) as a white solid. MS 292.1 [M+H].

Synthesis of 109. A mixture of 108 (13.4 g, 45.9 mmol) and NaBH$_4$ (10.4 g, 275.3 mmol) in ethanol (260 mL) was stirred at room temperature for 16 h. The reaction mixture was concentrated in vacuo and and the residue was dissolved with DCM (500 mL), washed with brine (100 mL×3), dried over anhydrous Na$_2$SO$_4$ and then concentrated in vacuo. The residue was purified by column chromatography on silica gel (DCM:MeOH=100:1~20:1) to give 109 (8.6 g, 750%) as a white solid. MS 251.4 [M+H]$^+$.

Synthesis of 110. To a mixture of 109 (8.6 g, 34.4 mmol) in DMF (200 mL) at room temperature was added NaH (60% in mineral oil) (4.1 g, 103.2 mmol). The resulting mixture was stirred at room temperature for 30 min, whereupon MeI (14.6 g, 103.2 mmol) was added dropwise. The resulting reaction mixture was stirred at room temperature for 1 h, and the solution was then diluted with water (300 mL), and extracted with EtOAc (200 mL×3). The combined organic layer was washed with brine (100 mL×3), dried over anhydrous Na$_2$SO$_4$ and then concentrated in vacuo. The residue was purified by column chromatography on silica gel (PE:EtOAc=8:1~3:1) to give 110 (8.0 g, 88%) as an off-white solid. MS 265.3 [M+H]$^+$.

Synthesis of 111. To a solution of 110 (7.6 g, 28.8 mmol) in DCM (70 mL) in an ice bath was added TFA (38 mL) dropwise. The resulting solution was stirred at room temperature for 1 h, whereupon the solvent was removed in vacuo to give 111 as a crude product. MS 165.2 [M+H]$^+$.

Synthesis of 112. A mixture of 111 (28.8 mmol, crude product from last step), A3 (11.8 g, 24 mmol) and Na$_2$CO$_3$ (25.4 g, 240 mmol) in DMSO (200 mL) was stirred at room temperature for 16 h. When the reaction had reached completion, as indicated by LCMS, the solution was diluted with water (300 mL), and then extracted with EtOAc (200 mL×3). The combined organic layers were washed with brine (100 mL×3), dried over anhydrous Na$_2$SO$_4$ and then concentrated in vacuo. The residue was purified by column chromatography on silica gel (PE:EtOAc=1:1 to EtOAc) to give 112 (7.0 g, 66%) as a yellow solid. MS 442.2 [M+H]$^+$.

Synthesis of Compound 2. A mixture of 112 (7.0 g, 15.9 mmol) and Pd/C (2.3 g) in DCM/MeOH (140 mL/140 mL) was stirred at room temperature for 2 h under a H$_2$ atmosphere. Pd/C was then removed by filtration through the Celite. The filtrate was concentrated and the residue was recrystallized with MTBE to give Compound 2 (4.5 g, 69%) as a light yellow solid. MS 412.1 [M+H]$^+$.

Example 3. Synthesis of Compound 3
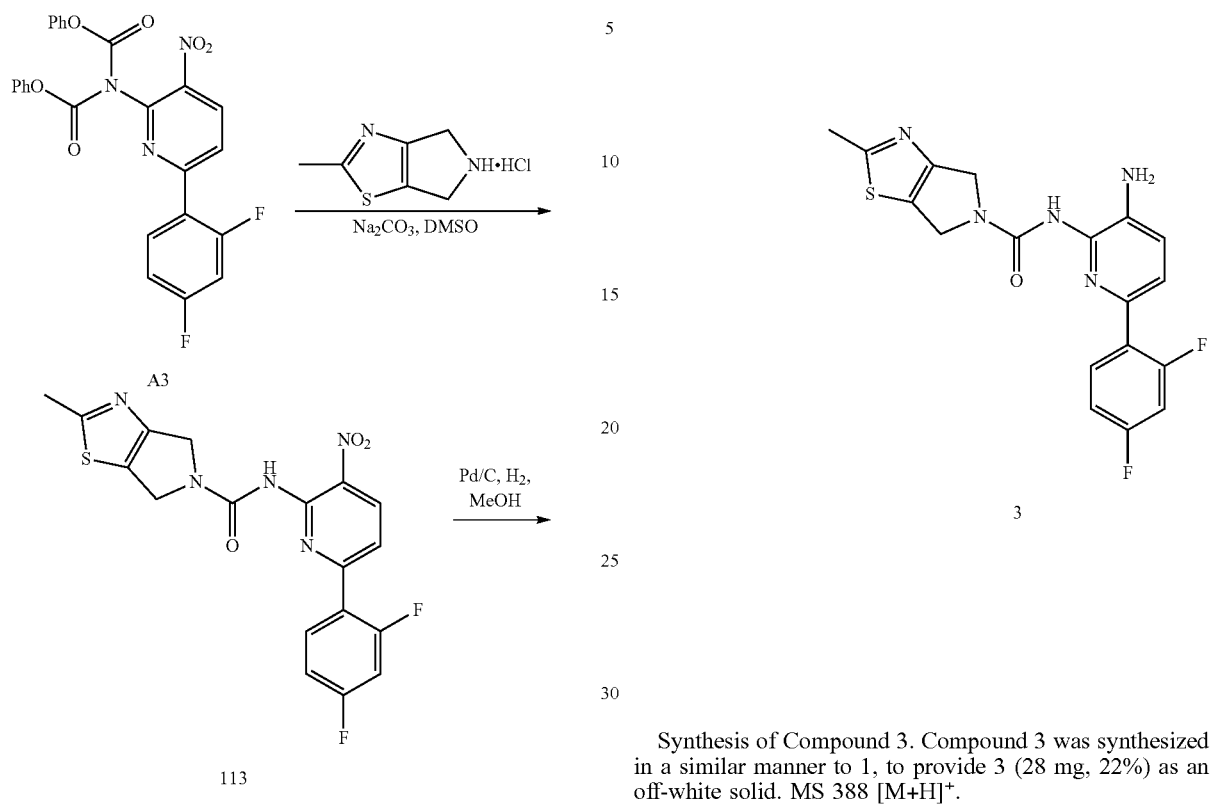
Synthesis of Compound 3. Compound 3 was synthesized in a similar manner to 1, to provide 3 (28 mg, 22%) as an off-white solid. MS 388 [M+H]$^+$.
Example 4. Synthesis of Compound 4
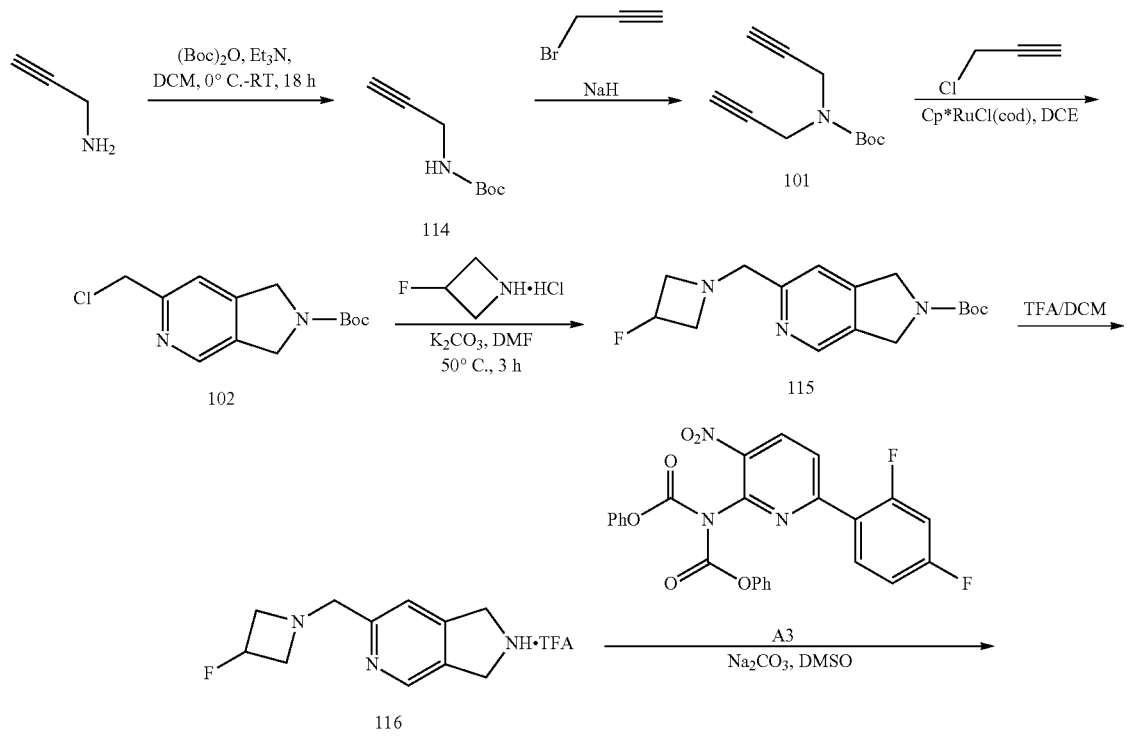

-continued

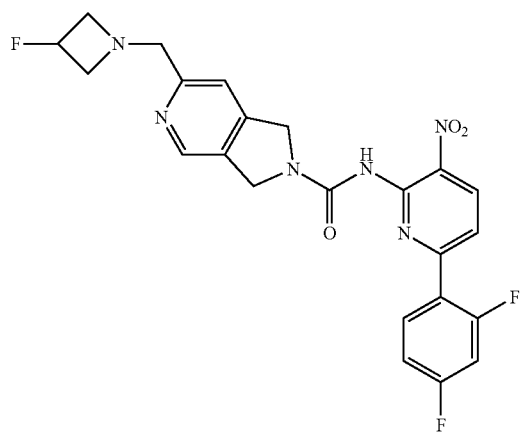

117

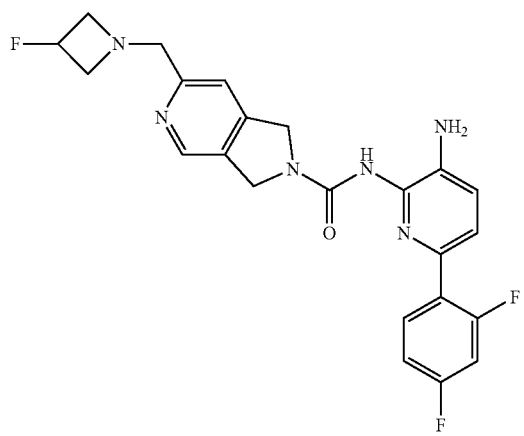

4

Synthesis of 114. To a solution of prop-2-yn-1-amine (5.0 g, 90.9 mmol) and Et₃N (18.4 g, 181.8 mmol) in DCM (100 mL) cooled with an ice bath was added (Boc)₂O (23.8 g, 109.1 mmol) dropwise. Upon completion of addition of (Boc)₂O, the resulting mixture was allowed to warm to room temperature, and was stirred at room temperature for 16 h. When the reaction was complete, the mixture was diluted with DCM (200 mL), and then washed with brine (100 mL×3). The organic layer was dried over Na₂SO₄ and then concentrated in vacuo. The residue was purified by column chromatography on silica gel (PE:EtOAc=100: 1~10:1) to give 114 (10 g, 71%) as a colorless oil. MS 178.3 [M+23]⁺, 100.3 [M−56]⁺.

Synthesis of 101. To a solution of 114 (10 g, 64.5 mmol) in DMF (200 mL) was added NaH (60% in mineral oil) (2.84 g, 71 mmol) slowly while the reaction mixture was cooled with an ice bath. The resulting reaction mixture was stirred at room temperature for 1 h, and then 3-bromoprop-1-yne (9.2 g, 77.4 mmol) was added into the above mixture and stirred at room temperature for 2 h. The reaction was then quenched with water (500 mL) and extracted with t-BuOMe (250 mL×3). The combined organic layer was washed with brine (200 mL×3), dried over anhydrous Na₂SO₄ and then concentrated in vacuo. The residue was purified by column chromatography on silica gel (PE:EtOAc=100:1~10:1) to give 101 (12 g, 96%) as a yellow oil. MS 138.1 [M−56]⁺.

Synthesis of 102. To a solution of 2-chloroacetonitrile (3.13 g, 41.4 mmol) and [Cp*RuCl(cod)] (394 mg, 1.0 mmol) in DCE (40 mL) was added a solution of 101 (4.0 g, 20.7 mmol) in DCE (80 mL) dropwise over 30 min under N₂ atmosphere. The resulting reaction mixture was stirred at 40° C. for 16 h. The solvent was then removed in vacuo, and the crude residue was purified by column chromatography on silica gel (PE:EtOAc=10:12:1) to give 102 (2.1 g, 22%) as a tan solid. MS 269.3 [M+H]⁺.

Synthesis of 115. A mixture of 102 (1.50 g, 5.6 mmol), 3-fluoroazetidine hydrochloride (932 mg, 8.4 mmol) and K₂CO₃ (2.32 g, 16.8 mmol) in DMF (30 mL) was stirred at 50° C. for 3 h. The mixture was then diluted with water (60 mL) and extracted with EtOAc (30 mL×4). The combined organic layers were washed with brine (30 mL×3), dried over anhydrous Na₂SO₄ and then concentrated in vacuo. The residue was purified by column chromatography on silica gel (DCM:MeOH=100:1~30:1) to give 115 (1.4 g, 81%) as a white solid. MS 308.2 [M+H]⁺.

Synthesis of 116. To a solution of 115 (200 mg, 0.65 mmol) in DCM (4 mL) was added TFA (2 mL), and the resulting reaction mixture was stirred at room temperature for 1 h. When LCMS indicated that the reaction was finished, the solvent was removed in vacuo to give 116 as a crude product which was used without further purification in the next step. MS 208.2 [M+H]⁺.

Synthesis of 117. A mixture of A3 (265 mg, 0.54 mmol) and 116 (0.65 mmol, crude product from last step) in DMSO (40 mL) was stirred at room temperature for 10 min, and then Na₂CO₃ (458 mg, 4.32 mmol) was added. The resulting reaction mixture was stirred at room temperature for 2 h, then was diluted with water (80 mL), and extracted with EtOAc (40 mL×4). The combined organic layers were washed with brine (40 mL×3), dried over anhydrous Na₂SO₄ and then concentrated in vacuo. The residue was purified by column chromatography on silica gel (DCM:MeOH=100: 1~50:1) to give 117 (200 mg, 76%) as a yellow solid. MS 485.2 [M+H]⁺.

Synthesis of Compound 4. A mixture of 117 (200 mg, 0.41 mmol) and Pd/C (200 mg) in MeOH (8 mL) was stirred at room temperature for 1 h under H₂ atmosphere. The Pd/C was removed by filtration through the Celite, and the filtrate was concentrated to provide a crude residue, which was purified by Prep-TLC (DCM:MeOH=10:1) three times to give Compound 4 (26 mg, 14%) as a yellow solid.

Example 5. Synthesis of Compound 5

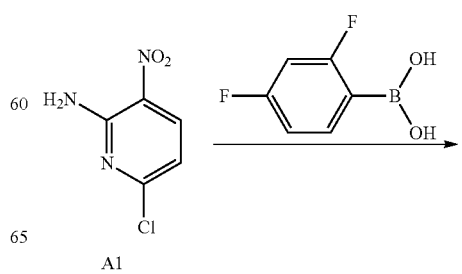

A1

-continued

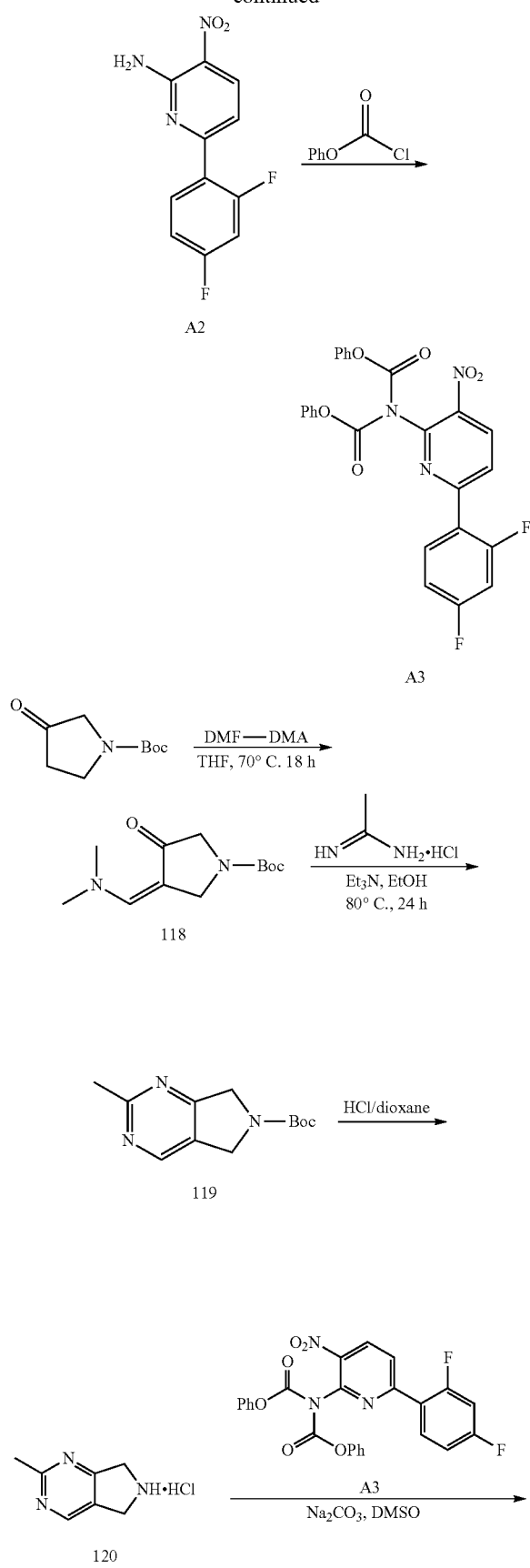

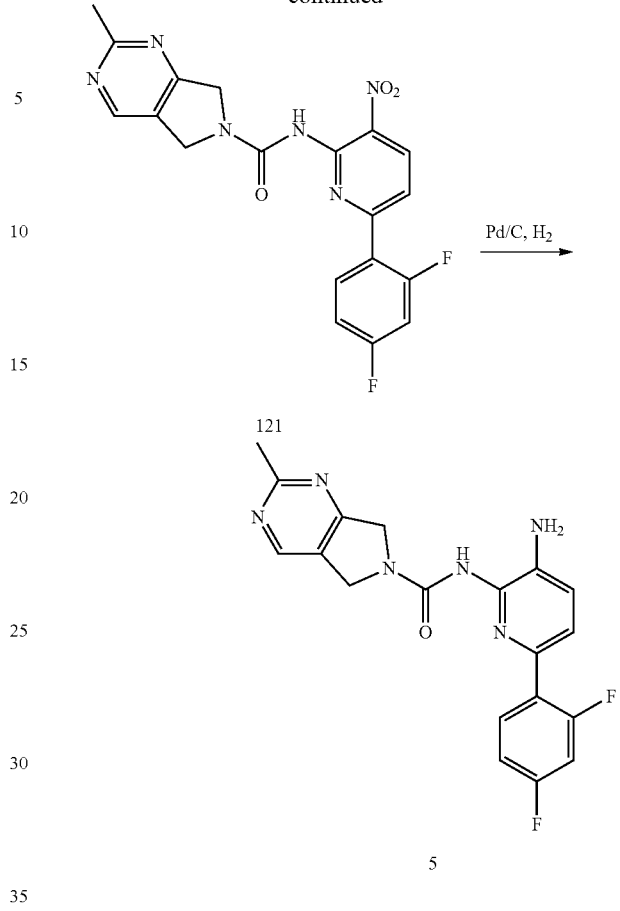

Synthesis of A2. A mixture of 6-chloro-3-nitropyridin-2-amine (4.58 g, 26.4 mmol), 2,4-difluorophenylboronic acid (5.00 g, 31.7 mmol) and Cs$_2$CO$_3$ (25.73 g, 79.2 mmol) in dioxane/H$_2$O (100 mL/10 mL) was treated with Pd(PPh$_3$)$_4$ (1.10 g, 0.95 mmol) under a N$_2$ atmosphere. The mixture was stirred at 100° C. for 2 h and then concentrated in vacuo. The residue was dissolved in EtOAc (200 mL), and the solution was washed with brine (100 mL×3). The organic layer was dried over anhydrous Na$_2$SO$_4$ and then concentrated in vacuo. The residue was purified by column chromatography on silica gel (PE:EtOAc=7:1~5:1) to give A2 (4.0 g, 61%) as a yellow solid. MS 252.1 [M+H]$^+$.

Synthesis of A3. A stirring solution of A2 (4.0 g, 15.94 mmol) in pyridine (60 mL) was treated with phenyl carbonochloridate (7.50 g, 47.81 mmol) dropwise at 0° C. After the addition was completed, the reaction mixture was stirred at 50° C. for 4 h. The mixture was then concentrated in vacuo, and the crude residue was purified by column chromatography on silica gel (PE:DCM=3:2~1:1) to give A3 (7.1 g, 91%) as a yellow solid. MS 492.1 [M+H]$^+$.

Synthesis of 118. A solution of tert-butyl 3-oxopyrrolidine-1-carboxylate (15.0 g, 81.1 mmol) and DMF-DMA (29.0 g, 243.3 mmol) in THF (150 mL) was stirred at 70° C. for 16 h. The solution was concentrated in vacuo to give 118 as a crude product which was used directly in the next step. MS 241.1 [M+H]$^+$.

Synthesis of 119. To a solution of 118 (81.1 mmol, crude product from last step) in EtOH (100 mL) was added Et$_3$N (40.4 g, 0.4 mol) and acetimidamide hydrochloride (30.1 g, 0.32 mol). The resulting solution was stirred at 80° C. for 24 h. After the solvent was removed in vacuo, the residue was diluted with water (100 mL) and extracted with DCM (50 mL×3). The combined organic layers were washed with brine (50 mL×3), dried over anhydrous Na₂SO₄ and then concentrated in vacuo. The residue was purified by column chromatography on silica gel (PE:DCM=10:1~1:2) to give 119 (10.5 g, 55%) as a brown solid. MS 236.2 [M+H]⁺.

Synthesis of 120. A solution of 119 (600 mg, 2.55 mmol) in dioxane/HCl (4 N, 10 mL) was stirred at room temperature for 1 h. The solution was concentrated in vacuo to give 120 (340 mg, 77%) as a white solid which was used without further purification. MS 136.2 [M+H]⁺.

Synthesis of 121. A mixture of A3 (231 mg, 0.47 mmol) and 120 (160 mg, 0.94 mmol) in DMSO (5 mL) was stirred at room temperature for 10 min. Then Na₂CO₃ (399 mg, 3.76 mmol) was added into above mixture and the resulting mixture was stirred at room temperature for 2 h. After the reaction had gone to completion, as indicated by LCMS, the reaction mixture was diluted with water (30 mL) and extracted with EtOAc (10 mL×3). The combined organic layers were washed with brine (10 mL×3), dried over anhydrous Na₂SO₄ and then concentrated in vacuo. The crude residue was purified by column chromatography on silica gel (DCM:MeOH=100:1~50:1) to provide 121 (120 mg, 62%) as a yellow solid. MS 413.2 [M+H]⁺.

Synthesis of Compound 5. A mixture of 121 (120 mg, 0.29 mmol) and Pd/C (120 mg) in MeOH (5 mL) was stirred at room temperature for 30 min under a H₂ atmosphere. The Pd/C was then removed by filtration through the Celite, the filtrate was concentrated, and the resulting crude residue was purified by Prep-TLC (DCM:MeOH=10:1) to give Compound 5 (52 mg, 47%) as a white solid. MS 383.2 [M+H]⁺, 405.0 [M+Na]⁺.

Example 6. Synthesis of Compound 6

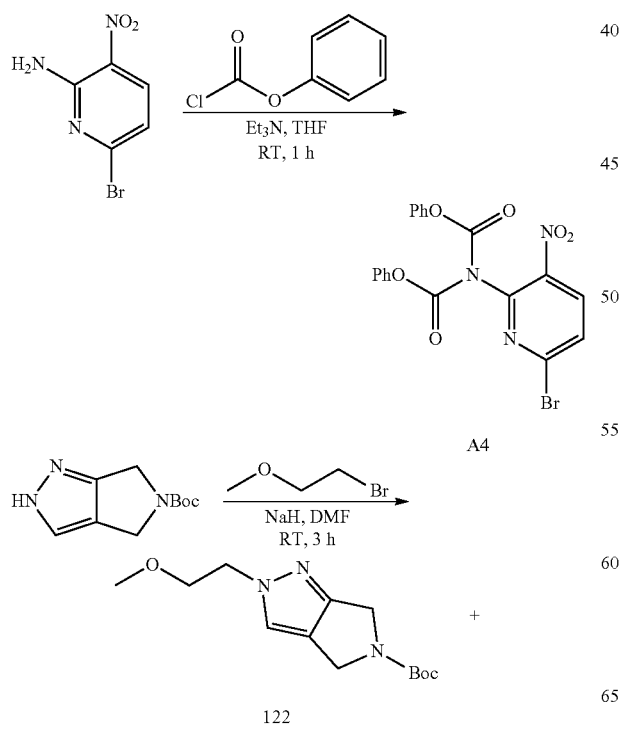

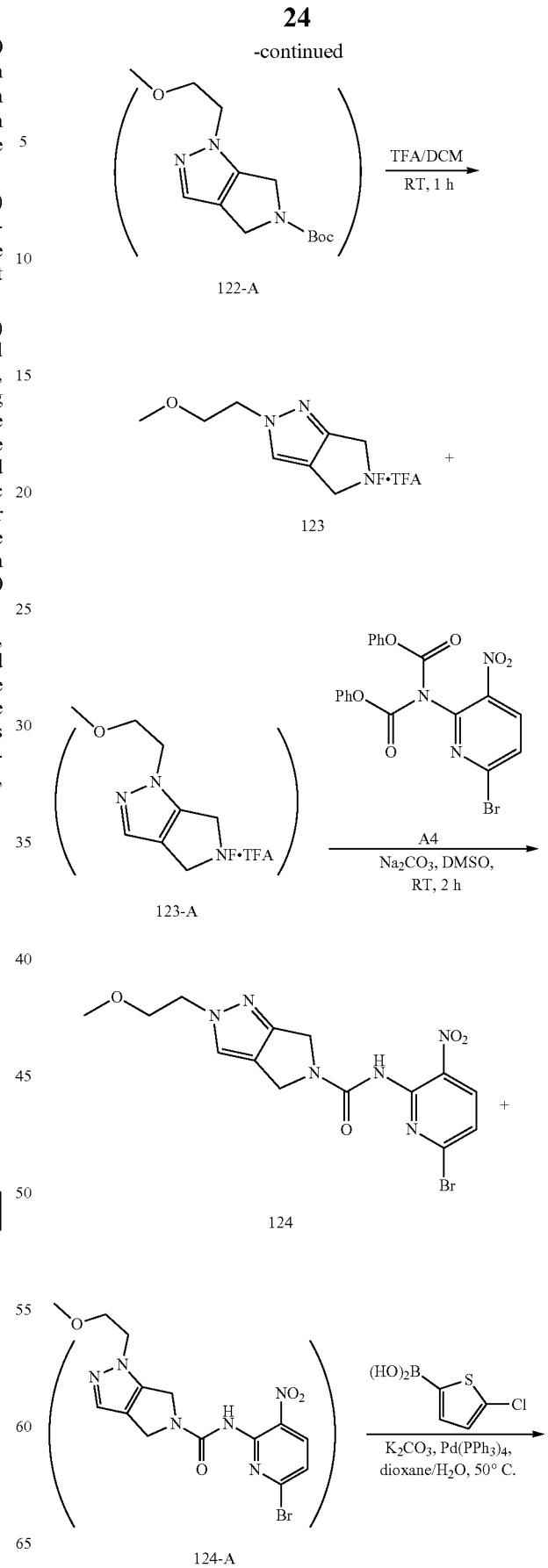

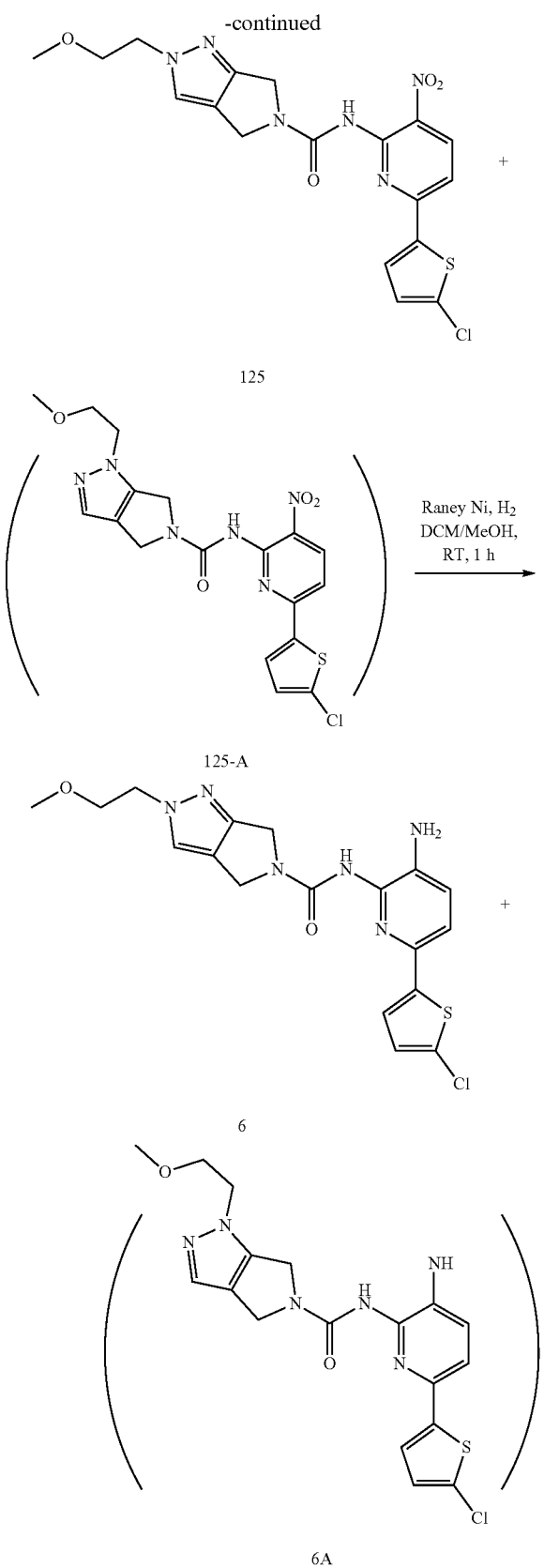

Synthesis of A4. A stirred solution of 6-bromo-3-nitropyridin-2-amine (5.0 g, 23.0 mmol) and Et$_3$N (6.9 g, 69.0 mmol) in THF (60 mL) was treated with phenyl carbonochloridate (10.8 g, 69.0 mmol) dropwise at 0° C. After the addition was completed, the mixture was stirred at room temperature for 1 h. The reaction mixture was then filtered and concentrated in vacuo. The resulting crude residue was recrystallized from petroleum ether to give A4 (10.2 g, 97%) as a light yellow solid. MS 458.0, 460.0 [M+H]$^+$.

Synthesis of 122 and 122-A. To a solution of tert-butyl 4,6-dihydropyrrolo[3,4-c]pyrazole-5(2H)-carboxylate (15.0 g, 71.8 mmol) in DMF (150 mL) was added NaH (60% in mineral oil) (8.6 g, 215.4 mmol) while the reaction mixture was cooled with an ice bath. When the addition was complete, the resulting mixture was allowed to warm to room temperature and was stirred at room temperature for 30 min. At this point, 1-bromo-2-methoxyethane (19.8 g, 143.6 mmol) was added into the reaction mixture, and stirring was continued at room temperature for 2 h. The reaction mixture was then quenched with water (300 mL), and extracted with EtOAc (150 mL×3). The combined organic layer was washed with brine (100 mL×3), dried over anhydrous Na$_2$SO$_4$ and then concentrated in vacuo. The residue was purified by column chromatography on silica gel (DCM:MeOH=100:1~30:1) to give a mixture of 122 and 122-A (19.0 g, 99%) as a colorless oil. MS 268.2 [M+H]$^+$.

Synthesis of 123 and 123-A. To a solution of 122 and 122-A (6.5 g, 24.3 mmol) in DCM (60 mL) cooled with an ice bath was added TFA (30 mL). The reaction mixture was stirred at room temperature for 1 h, whereupon the solvent was removed in vacuo to give 123 and 123-A as a crude product mixture which was used directly in the next step without further purification. MS 168.1 [M+H]$^+$.

Synthesis of 124 and 124-A. To a solution of 123 and 123-A (24.3 mmol, crude product from last step) and A4 (9.3 g, 20.3 mmol) in DMSO (200 mL) was added Na$_2$CO$_3$ (21.5 g, 203 mmol), and the reaction mixture was stirred at room temperature for 4 h. The mixture was then diluted with water (400 mL) and extracted with EtOAc (200 mL×3). The combined organic layers were washed with brine (100 mL×3), dried over anhydrous Na$_2$SO$_4$ and then concentrated in vacuo. The residue was purified by column chromatography on silica gel (DCM:MeOH=100:1~30:1) to give a mixture of 124 and 124-A (4.5 g, 50%) as a yellow solid. MS 411.0, 413.1 [M+H]$^+$.

Synthesis of 125 and 125-A. A mixture of 124 and 124-A (500 mg, 1.22 mmol), 5-chlorothiophen-2-ylboronic acid (237 mg, 1.46 mmol) and K$_2$CO$_3$ (169 mg, 1.23 mmol) in dioxane/H$_2$O (10 mL/2 mL) was treated with Pd(PPh$_3$)$_4$ (45 mg, 0.06 mmol) under a N$_2$ atmosphere. The reaction mixture was stirred at 50° C. for 3 h and then concentrated in vacuo. The residue was taken up in EtOAc (30 mL), and the resulting solution was washed with brine (10 mL×3). The organic layer was then dried over anhydrous Na$_2$SO$_4$ and concentrated in vacuo. The crude residue was purified by Prep-TLC (DCM:MeOH=20:1) to give a mixture of 125 and 125-A (450 mg, 82%) as a yellow solid. MS 449.2 [M+H]$^+$.

Synthesis of Compound 6 and Compound 6A. A mixture of 125 and 125-A (450 mg, 1.0 mmol) and Raney Ni (100 mg) in DCM/MeOH (6 mL/6 mL) was stirred at room temperature for 1 h under a H$_2$ atmosphere. Raney Ni was then removed by filtration through Celite, the filtrate was concentrated en vacuo, and the residue was purified by Prep-TLC (DCM:MeOH=10:1). The mixture of regioisomers was then separated by using chiral HPLC (Column: Chiralcel OD-3; Solvent: MeOH; Flow rate: 2 mL/min; RT$_{1843}$=3.477 min, RT$_{1843A}$=4.142 min) to give Compound 6 (99 mg, 24%) as a white solid (MS 419.2 [M+H]⁺) and Compound 6A (50 mg, 12%) as a white solid. MS 419.2 [M+H]⁺.

Example 7. Synthesis of Compound 7

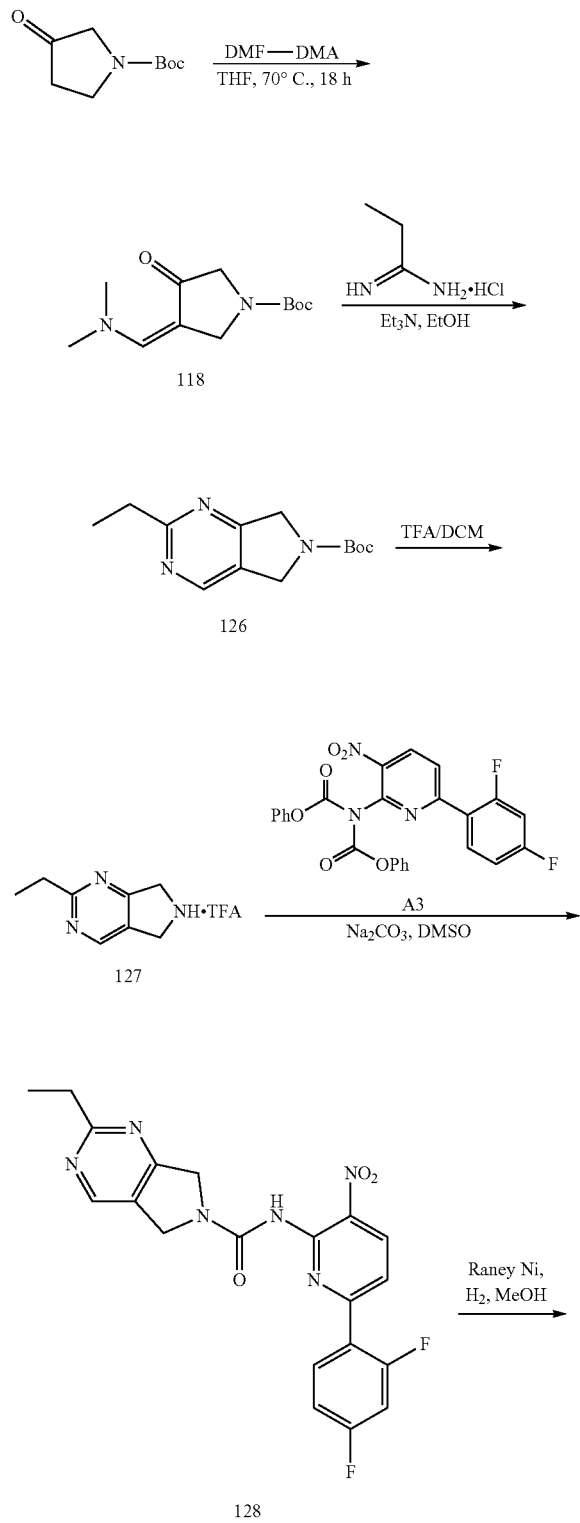

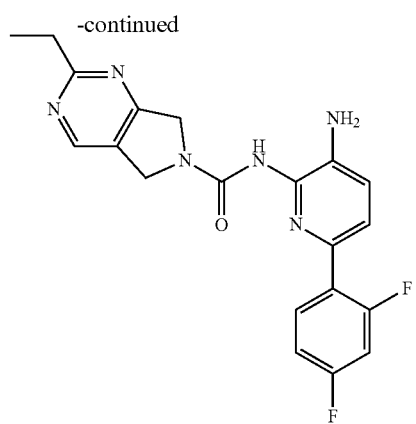

Synthesis of 118. A solution of tert-butyl 3-oxopyrrolidine-1-carboxylate (600 mg, 3.24 mmol) and DMF-DMA (1.2 g, 9.72 mmol) in THF (10 mL) was stirred at 70° C. for 16 h. The solution was concentrated in vacuo to give 118 as a crude product which was used directly in the next step. MS 241.1 [M+H]⁺.

Synthesis of 126. To a solution of 118 (3.24 mmol, crude product from last step) in EtOH (10 mL) was added Et₃N (1.6 g, 16.2 mol) and propionimidamide hydrochloride (1.4 g, 13.0 mmol). The resulting solution was stirred at 80° C. for 20 h, whereupon the solvent was removed in vacuo, the residue was diluted with water (10 mL), and the mixture was then extracted with DCM (10 mL×3). The combined organic layers were washed with brine (10 mL×3), dried over anhydrous Na₂SO₄ and then concentrated in vacuo. The residue was purified by column chromatography on silica gel (PE:DCM=10:1~1:2) to give 126 (450 mg, 56%) as a brown solid. MS 250.2 [M+H]⁺.

Synthesis of 127. A solution of 126 (300 mg, 1.2 mmol) in DCM (6 mL) was treated with TFA (3 mL), and the reaction mixture was stirred at room temperature for 1 h. After 1 h, the reaction was complete, as indicated by LCMS, and the reaction mixture was concentrated in vacuo to give 127 as a crude product which was used directly in the next step without further purification. MS 150.2 [M+H]⁺.

Synthesis of 128. A mixture of A3 (294 mg, 0.6 mmol) and 127 (1.2 mmol, crude product from last step) in DMSO (10 mL) was stirred at room temperature for 10 min. Then Na₂CO₃ (636 mg, 6.0 mmol) was added, and the resulting mixture was stirred at room temperature for 2 h. After the reaction was complete, as indicated by LCMS, the reaction mixture was diluted with water (30 mL) and extracted with EtOAc (10 mL×3). The combined organic layers were washed with brine (10 mL×3), dried over anhydrous Na₂SO₄ and then concentrated in vacuo. The residue was purified by column chromatography on silica gel (DCM:MeOH=100:1~50:1) to provide 128 (136 mg, 53%) as a yellow solid. MS 427.2 [M+H]⁺.

Synthesis of Compound 7. A mixture of 128 (120 mg, 0.28 mmol) and Raney Ni (120 mg) in MeOH (5 mL) was stirred at room temperature for 1 h under a H₂ atmosphere. The Raney Ni was then removed by filtration through Celite, the filtrate was concentrated, and the crude residue was purified by Prep-TLC (DCM:MeOH=10:1) to give Compound 7 (80 mg, 72%) as a yellow solid. MS 397.1 [M+H]⁺.

Example 8. Synthesis of Compound 8

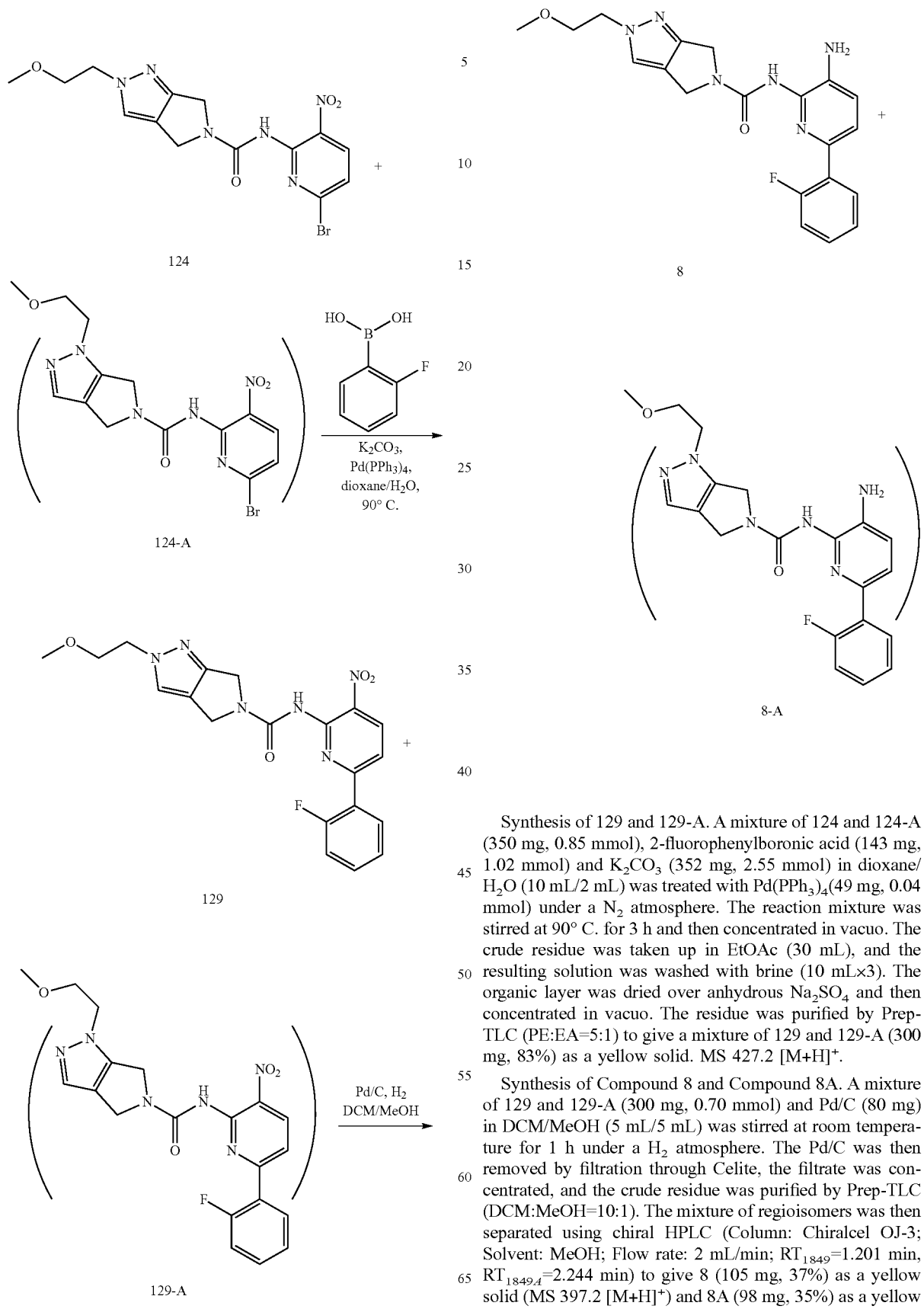

Synthesis of 129 and 129-A. A mixture of 124 and 124-A (350 mg, 0.85 mmol), 2-fluorophenylboronic acid (143 mg, 1.02 mmol) and $K_2CO_3$ (352 mg, 2.55 mmol) in dioxane/$H_2O$ (10 mL/2 mL) was treated with $Pd(PPh_3)_4$ (49 mg, 0.04 mmol) under a $N_2$ atmosphere. The reaction mixture was stirred at 90° C. for 3 h and then concentrated in vacuo. The crude residue was taken up in EtOAc (30 mL), and the resulting solution was washed with brine (10 mL×3). The organic layer was dried over anhydrous $Na_2SO_4$ and then concentrated in vacuo. The residue was purified by Prep-TLC (PE:EA=5:1) to give a mixture of 129 and 129-A (300 mg, 83%) as a yellow solid. MS 427.2 [M+H]$^+$.

Synthesis of Compound 8 and Compound 8A. A mixture of 129 and 129-A (300 mg, 0.70 mmol) and Pd/C (80 mg) in DCM/MeOH (5 mL/5 mL) was stirred at room temperature for 1 h under a $H_2$ atmosphere. The Pd/C was then removed by filtration through Celite, the filtrate was concentrated, and the crude residue was purified by Prep-TLC (DCM:MeOH=10:1). The mixture of regioisomers was then separated using chiral HPLC (Column: Chiralcel OJ-3; Solvent: MeOH; Flow rate: 2 mL/min; $RT_{1849}$=1.201 min, $RT_{1849A}$=2.244 min) to give 8 (105 mg, 37%) as a yellow solid (MS 397.2 [M+H]$^+$) and 8A (98 mg, 35%) as a yellow solid. MS 397.2 [M+H]$^+$.

Example 9. Synthesis of Compound 9

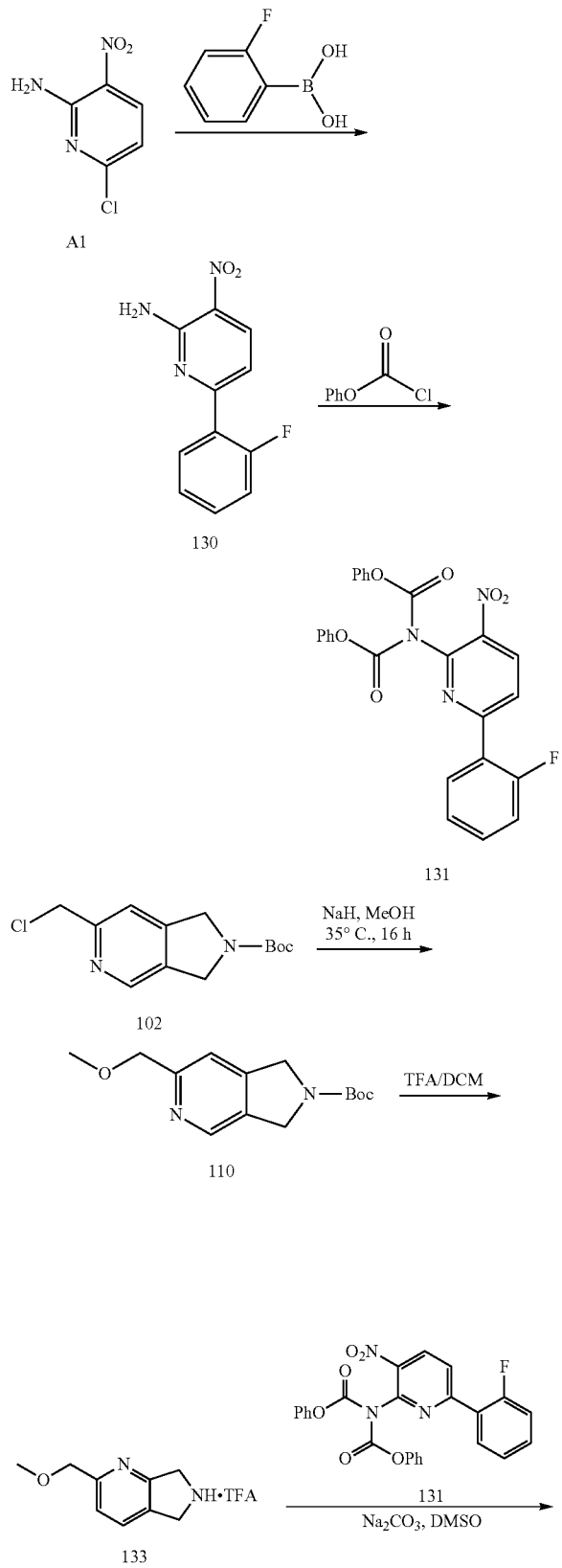

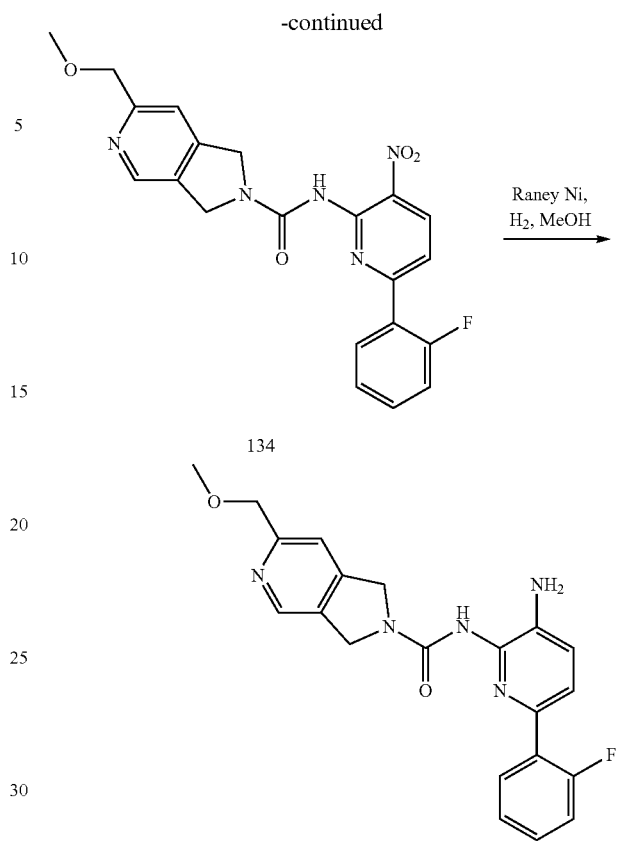

Synthesis of 130. A mixture of 6-chloro-3-nitropyridin-2-amine (0.5 g, 2.9 mmol), 2-fluorophenylboronic acid (487 mg, 3.48 mmol) and $K_2CO_3$ (1.20 g, 8.7 mmol) in dioxane/$H_2O$ (10 mL/1 mL) was treated with $Pd(PPh_3)_4$ (17 mg, 0.01 mmol) under a $N_2$ atmosphere. The reaction mixture was stirred at 90° C. for 2 h and then concentrated in vacuo. The crude residue was taken up in EtOAc (200 mL), and the resulting solution was washed with brine (100 mL×3). The organic layer was then dried over anhydrous $Na_2SO_4$ and concentrated in vacuo. The residue was purified by column chromatography on silica gel (PE:EtOAc=10:1~3:1) to give 130 (301 mg, 45%) as a yellow solid. MS 234.2 $[M+H]^+$.

Synthesis of 131. To a stirred solution of 130 (301 mg, 1.3 mmol) in pyridine (10 mL) was added phenyl carbonochloridate (608 mg, 3.9 mmol) dropwise while the reaction mixture was cooled with an ice bath. The resulting reaction mixture was stirred at 55° C. for 4 h, whereupon the reaction mixture was concentrated in vacuo. The resulting crude residue was purified by column chromatography on silica gel (PE:EtOAc=8:1~3:1) to give 131 (500 mg, 82%) as a yellow solid. MS 474.2 $[M+H]^+$.

Synthesis of 132. To an ice bath-cooled flask of MeOH (30 mL) was treated with NaH (60% in mineral oil) (940 mg, 23.5 mmol), and the reaction mixture was stirred at 0° C. for 30 min. Compound 102 (2.1 g, 7.8 mmol) was then added, and the reaction mixture was stirred at 35° C. for 16 h. At this point, the reaction mixture was quenched with water (30 mL), extracted with DCM (10 mL×3), and the combined organic layers were washed with brine (10 mL×3), dried over anhydrous $Na_2SO_4$ and then concentrated in vacuo. The resulting crude residue was purified by column chromatography on silica gel (PE:EtOAc=100:1~10:1) to give 132 (1.8 g, 94%) as a beige colored solid. MS 265.1 [M+H]+.

Synthesis of 133. To a solution of 132 (220 mg, 0.83 mmol) in DCM (6 mL) was added TFA (2 mL) dropwise, with the reaction mixture cooled in an ice bath. The reaction was stirred at room temperature 1 h, whereupon the solvent was removed in vacuo to give 133 as a crude product which was used directly in the next step. MS 165.1 [M+H]+.

Synthesis of 134. A mixture of 131 (313 mg, 0.64 mmol) and 133 (0.83 mmol, crude product from last step) in DMSO (10 mL) was treated with Na2CO3 (678 mg, 6.4 mmol), and the reaction mixture was then stirred at room temperature for 2 h. At this point, the reaction mixture was diluted with water (20 mL) and extracted with EtOAc (20 mL×3). The combined organic layers were washed with brine (20 mL×3), dried over anhydrous Na2SO4 and then concentrated in vacuo. The residue was purified by column chromatography on silica gel (EA to EA:MeOH=50:1) to give 134 (200 mg, 74%) as a yellow solid. MS 424.0 [M+H]+.

Synthesis of Compound 9. A mixture of 134 (200 mg, 0.47 mmol) and Pd/C (200 mg) in DCM/MeOH (4 mL/4 mL) was stirred at room temperature for 1 h under a H2 atmosphere. The Pd/C was then removed by filtration through Celite, the filtrate was concentrated and the resulting crude residue was purified by Prep-TLC (DCM: MeOH=10:1) to give Compound 9 (105 mg, 57%) as a yellow solid. MS 394.2 [M+H]+.

Example 10. Synthesis of Compound 10

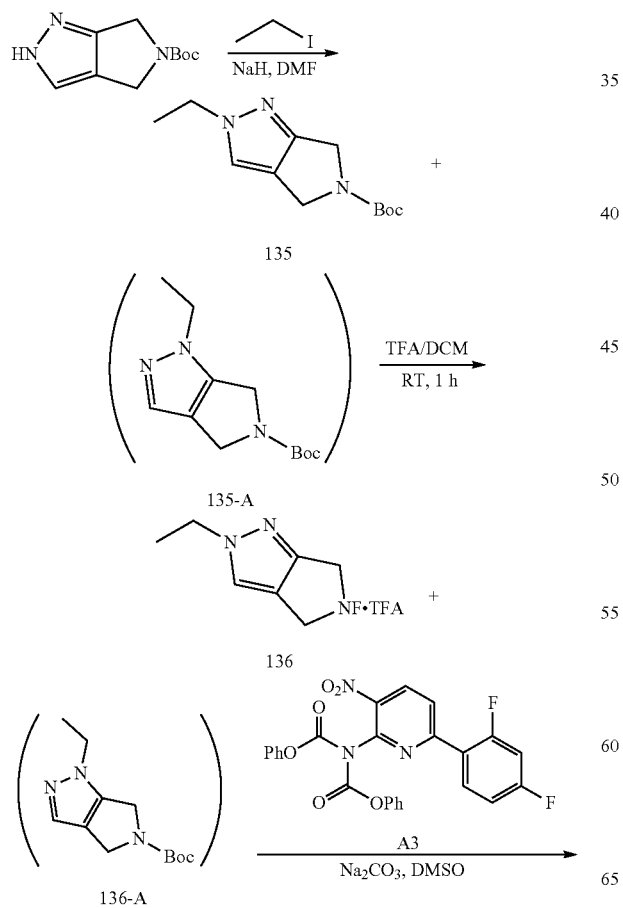

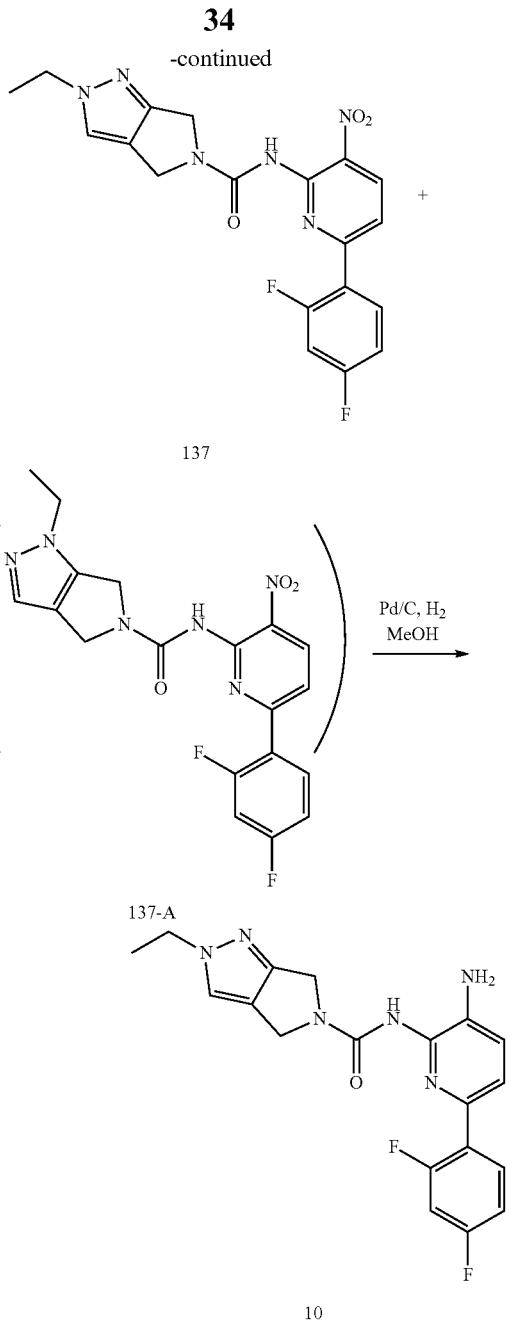

Synthesis of 135 and 135-A. To a solution of tert-butyl 4,6-dihydropyrrolo[3,4-c]pyrazole-5(2H)-carboxylate (250 mg, 1.2 mmol) in DMF (5 mL) was added NaH (96 mg, 2.4 mmol (60% in mineral oil)), with the reaction mixture being cooled with an ice bath. The resulting mixture was stirred at room temperature for 1 h, whereupon iodoethane (374 mg, 2.4 mmol) was added, and the resulting reaction mixture was stirred at room temperature for 2 h. The reaction mixture was then diluted with water (10 mL) and extracted with EtOAc (10 mL×3). The combined organic layers were washed with brine (10 mL×3), dried over anhydrous Na2SO4 and then concentrated in vacuo to give 135 and 135-A as a crude product. MS 238.2 [M+H]+.

Synthesis of 136 and 136-A. To a solution of 135 and 135-A (1.2 mmol, crude product from last step) in DCM (6 mL) was added TFA (2 mL) dropwise while the reaction mixture was cooled with an ice bath. The reaction mixture was stirred at room temperature 1 h, whereupon the solvent was removed in vacuo to give 136 and 136-A as a crude product which was used in the next step without further purification. MS 138.2 [M+H]+.

Synthesis of 137. A mixture of 136 and 136-A (1.2 mmol, crude product from last step) and A3 (491 mg, 1.0 mmol) in DMSO (10 mL) was stirred at room temperature for 10 min, then Na$_2$CO$_3$ (848 mg, 8.0 mol) was added, and the reaction mixture was stirred at room temperature for 2 h. The reaction mixture was then diluted with water (20 mL) and extracted with EtOAc (20 mL×3). The combined organic layers were washed with brine (20 mL×3), dried over anhydrous Na$_2$SO$_4$ and then concentrated in vacuo. The crude residue was purified by column chromatography on silica gel (DCM:MeOH=100:1~50:1) to give a crude product which was a mixture of the regioisomers 137 and 137-A. The crude product was further purified by Prep-TLC (DCM:MeOH=30:1) to give 137 (150 mg, 36%) as a yellow solid. MS 415.1 [M+H]+.

Synthesis of Compound 10. A mixture of 137 (150 mg, 0.36 mmol) and Pd/C (150 mg) in MeOH (5 mL) was stirred at room temperature for 1 h under a H$_2$ atmosphere. The Pd/C was then removed by filtration through Celite, the filtrate was concentrated and the residue was purified by Prep-TLC (DCM:MeOH=15:1) to give Compound 10 (85 mg, 61%) as a yellow solid. MS 385.1 [M+H]+.

TABLE 1

| | | | | |
|---|---|---|---|---|
| | Spectrometric Data for Compounds | | | |
| No. | Structure | MS Calc. | MS found | $^1$H NMR Data (400 MHz, DMSO-d$_6$) |
| 1 | 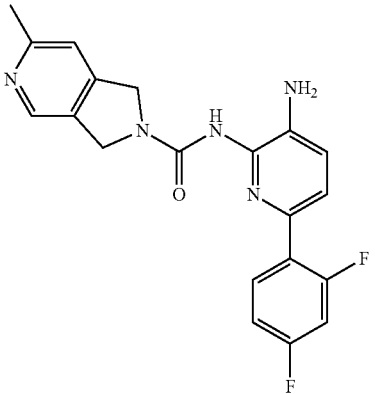 [SMILES: Cc1cc2c(cn1)CN(C(=O)Nc1nc(-c3ccc(F)cc3F)ccc1N)C2] | 381 | 382 | δ 2.48 (s, 3H), 4.77 (s, 4H), 5.28 (s, 2H), 7.16-7.18 (m, 2H), 7.28-7.31 (m, 2H), 7.40-7.42 (m, 1H), 7.92-7.94 (m, 1H), 8.45 (s, 1H), 8.56 (s, 1H). |
| 2 | 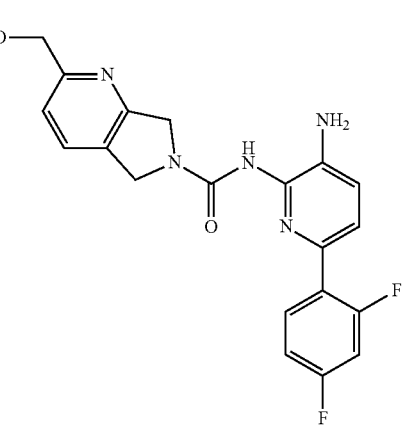 | 411 | 412 | δ 8.59 (s, 1H), 7.98-7.92 (m, 1H), 7.81 (d, J = 7.6 Hz, 1H), 7.43-7.40 (m, 1H), 7.36-7.26 (m, 2H), 7.18-7.14 (m, 2H), 5.28 (s, 2H), 4.77 (s, 4H), 4.51 (s, 2H), 3.37 (s, 3H). |
| 3 | 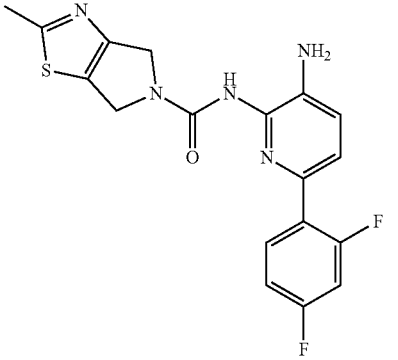 | 387 | 388 | δ 8.55 (s, 1H), 7.95 (q, J = 8.80 Hz, 1H), 7.42 (d, J = 2.40 Hz, 1H), 7.33-7.27 (m, 1H), 7.19-7.14 (m, 2H), 5.27 (s, 2H), 4.68 (d, J = 34.40 Hz, 4H), 2.70 (s, 3H). |

TABLE 1-continued

Spectrometric Data for Compounds

| No. | Structure | MS Calc. | MS found | ¹H NMR Data (400 MHz, DMSO-$d_6$) |
|---|---|---|---|---|
| 4 | 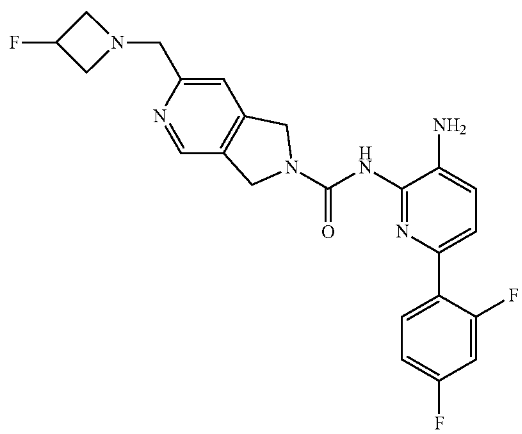 [SMILES: Nc1ccc(-c2ccc(F)cc2F)nc1NC(=O)N1Cc2cnc(CN3CC(F)C3)cc2C1] | 454 | 455 | δ 8.59 (s, 1H), 8.50 (s, 1H), 7.97-7.91 (m, 1H), 7.41 (dd, J = 8.0, 2.0 Hz, 1H), 7.37 (s, 1H), 7.33-7.27 (m, 1H), 7.19-7.14 (m, 2H), 5.29-5.26 (m, 2.5H), 5.14-5.12 (m, 0.5H), 4.80 (s, 4H), 3.76 (s, 2H), 3.66-3.58 (m, 2H), 3.28-3.24 (m, 1H), 3.22-3.19 (m, 1H). |
| 5 | 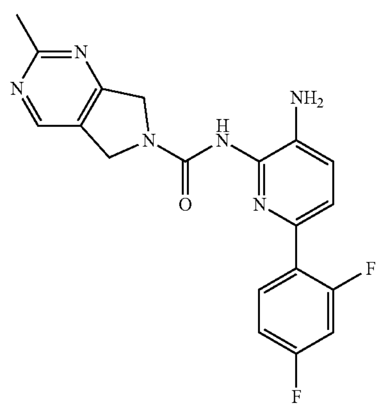 [SMILES: Cc1ncc2c(n1)CN(C(=O)Nc1nc(-c3ccc(F)cc3F)ccc1N)C2] | 382 | 383 | δ 8.70 (s, 1H), 8.65 (s, 1H), 7.97-7.91 (m, 1H), 7.42 (dd, J = 8.0, 2.0 Hz, 1H), 7.33-7.27 (m, 1H), 7.18-7.14 (m, 2H), 5.29 (s, 2H), 4.77 (d, J = 5.6 Hz, 4H), 2.64 (s, 3H). |
| 6 | 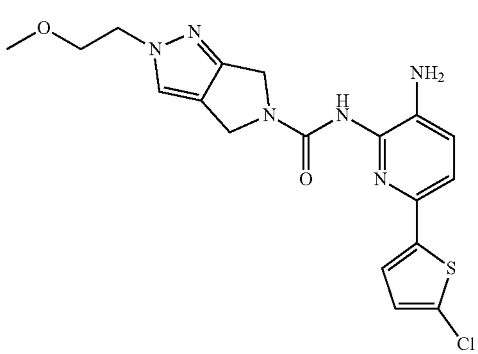 [SMILES: COCCn1cc2c(n1)CN(C(=O)Nc1nc(-c3ccc(Cl)s3)ccc1N)C2] | 418 | 419 | δ 8.41 (s, 1H), 7.56 (s, 1H), 7.51 (d, J = 8.4 Hz, 1H), 7.34 (d, J = 4.0 Hz, 1H), 7.12 (d, J = 8.4 Hz, 1H), 7.05 (d, J = 4.0 Hz, 1H), 5.24 (s, 2H), 4.50 (s, 4H), 4.26 (t, J = 5.2 Hz, 2H), 3.68 (t, J = 5.6 Hz, 2H), 3.24 (s, 3H). |

TABLE 1-continued

Spectrometric Data for Compounds

| No. | Structure | MS Calc. | MS found | ¹H NMR Data (400 MHz, DMSO-d$_6$) |
|---|---|---|---|---|
| 7 | 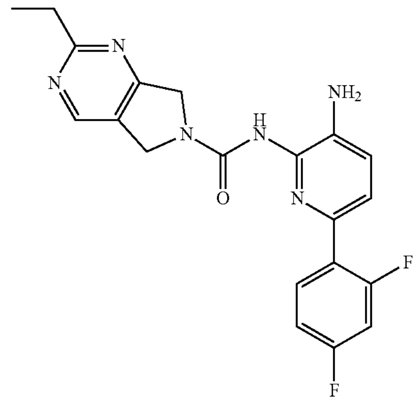 [SMILES: CCc1ncc2c(n1)CN(C(=O)Nc1nc(-c3ccc(F)cc3F)ccc1N)C2] | 396 | 396 | δ 8.73 (s, 1H), 8.64 (s, 2H), 7.97-7.91 (m, 1H), 7.42 (dd, J = 8.0, 3.0 Hz, 1H), 7.32-7.26 (m, 1H), 7.18-7.14 (m, 2H), 5.29 (s, 2H), 4.78 (d, J = 10.0 Hz, 4H), 2.92 (q, J = 7.6 Hz, 2H), 1.29 (t, J = 7.6 Hz, 3H). |
| 8 | 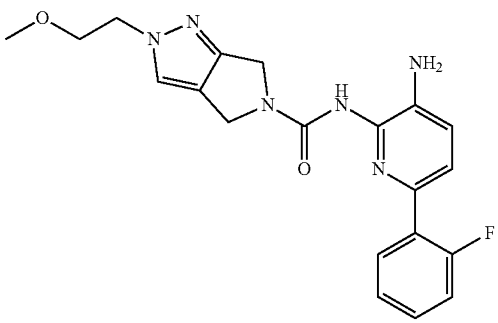 [SMILES: COCCn1cc2c(n1)CN(C(=O)Nc1nc(-c3ccccc3F)ccc1N)C2] | 396 | 397 | δ 8.47 (s, 1H), 7.93-7.89 (m, 1H), 7.57 (s, 1H), 7.45-7.43 (m, 1H), 7.35-7.28 (m, 1H), 7.25-7.22 (m, 2H), 7.17 (d, J = 8.4 Hz, 1H), 5.24 (s, 2H), 4.51 (s, 4H), 4.26 (t, J = 5.6 Hz, 2H), 3.68 (t, J = 5.2 Hz, 2H), 3.24 (s, 3H). |
| 9 | 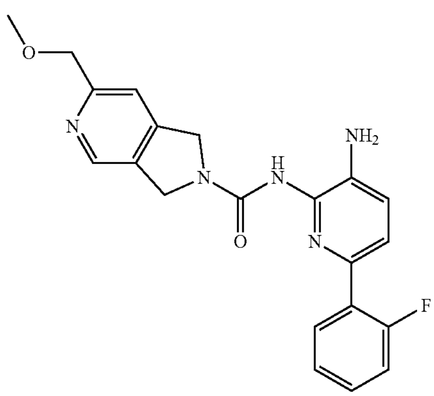 [SMILES: COCc1cc2c(cn1)CN(C(=O)Nc1nc(-c3ccccc3F)ccc1N)C2] | 393 | 394 | δ 8.58 (s, 1H), 8.53 (s, 1H), 7.93-7.89 (m, 1H), 7.46-7.44 (m, 2H), 7.35-7.32 (m, 1H), 7.28-7.22 (m, 2H), 7.17 (d, J = 8.4 Hz, 1H), 5.28 (s, 2H), 4.83 (s, 4H), 4.52 (s, 2H), 3.38 (s, 3H). |
| 10 | 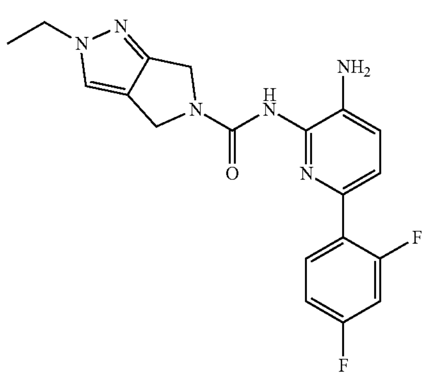 [SMILES: CCn1cc2c(n1)CN(C(=O)Nc1nc(-c3ccc(F)cc3F)ccc1N)C2] | 384 | 385 | δ 8.47 (s, 1H), 7.96-7.93 (m, 1H), 7.60 (s, 1H), 7.40 (dd, J = 8.0, 2.4 Hz, 1H), 7.32-7.26 (m, 1H), 7.18-7.14 (m, 2H), 5.25 (s, 2H), 4.52 (s, 4H), 4.13 (q, J = 7.2 Hz, 2H), 1.38 (t, J = 7.2 Hz, 3H), 3.24 (s, 3H). |

HDAC2 and HDAC1 Enzymatic Assay (HDAC2 IC50 Data)

The following describes an assay protocol for measuring the deacetylation of a peptide substrate by the enzymes HDAC2 or HDAC1. Enzyme, substrate, and cofactors are combined in a well of a microtiter plate and incubated for 3 hours at 25° C. At the end of the incubation, the reaction is quenched by the addition of an SDS-containing buffer. Substrate and product are separated and quantified electrophoretically using the microfluidic-based LabChip 3000 Drug Discovery System from Caliper Life Sciences. The peptide substrate used in this assay is FAM-TSRHK(AC)KL-CONH2 (FAM is carboxyfluorescein). Peptide should be >98% purity by Capillary Electrophoresis.

1. To a well of a 384-well plate, add 5 µL of 2×enzyme buffer. Using Labcyte Echo 550, add 100 nl compound. Enzyme and compound may be pre-incubated at this time if desired.
2. Add 5 µL of 2× substrate buffer.
3. Incubate plate at 25° C. for 17 hours.
4. Terminate reaction by adding 40 µL of 1.55× stop buffer.
5. Create job on a Caliper LabChip® 3000 Drug Discovery System.
6. Load the plate and start electrophoresis using blue laser (480 nm) for excitation and green CCD (520 nm) for detection (CCD2).

Reaction time=17 hours; Reaction temperature=25° C.

Final Assay Reaction Mixture 100 mM HEPES, pH 7.5 0.1% BSA 0.01% Triton X-100 25 mM KCl
1% DMSO (from compound) 1 µM FAM-TSRHK(AC)KL-CONH2 5 nM HDAC Enzyme (specific activity may vary from lot-to-lot, and enzyme concentration may need to be adjusted to yield ~10-20% conversion of substrate to product).

Substrate and product peptides present in each sample are separated electrophoretically using the LabChip 3000 capillary electrophoresis instrument. As substrate and product peptides are separated, two peaks of fluorescence are observed. Change in the relative fluorescence intensity of the substrate and product peaks is the parameter measured, reflecting enzyme activity. Capillary electrophoregramms (RDA acquisition files) are analyzed using HTS Well Analyzer software (Caliper Life Sciences). The enzyme activity in each sample is determined as the product to sum ratio (PSR):P/(S+P), where P is the peak height of the product peptide and S is the peak height of the substrate peptide. For each compound, enzyme activity is measured at various concentrations (12 concentrations of compound spaced by 3× dilution intervals). Negative control samples (0%-inhibition in the absence of inhibitor) and positive control samples (100%-inhibition, in the presence of 20 mM EDTA) are assembled in replicates of four and are used to calculate %-inhibition values for each compound at each concentration. Percent inhibition ($P_{inh}$) is determined using following equation: $P_{inh}=(PSR_0\%-PSR_{inh})/(PSR_0\%-PSR_{100}\%)*100$, where $PSR_{inh}$ is the product sum ratio in the presence of inhibitor, $PSR_0\%$ is the average product sum ration in the absence of inhibitor and $PSR_{100}\%$ is the average product sum ratio in 100%-inhibition control samples.

The IC50 values of inhibitors are determined by fitting the inhibition curves ($P_{inh}$ versus inhibitor concentration) by 4 parameter sigmoidal dose-response model using XLfit 4 software (IBDS).

The results of this assay for certain compounds are reported in Table 2, below. In the table, "A" indicates a $K_d$ value of less than 0.1 µM; "B" a $K_d$ value of between 0.1 µM and 0.5 µM; "C" a $K_d$ value of greater than 0.5 µM and less than or equal to 5.0 µM; and "D" a $K_d$ value of greater than 5.0 µM.

TABLE 2

| Compound No. | HDAC2 IC50, (uM) | HDAC1 IC50, (uM) |
|---|---|---|
| 1 | B | B |
| 2 | C | B |
| 3 | C | B |
| 4 | C | B |
| 5 | C | C |
| 6 | C | C |
| 7 | C | B |
| 8 | C | B |
| 9 | C | B |
| 10 | B | B |

HDAC2 Enzymatic Inhibition Assay in SH-SY5Y Cell Lysate

Cell Culture and Inhibitor Treatments

SH-SY5Y cells (Sigma) were cultured in Eagle's Modified Essential Medium supplemented with 10% fetal bovine serum and pen/strep. Twenty-four hours prior to compound dosing 20 uL of cells were plated in white 384 well plates at a density of 1,500 cells/well. Compounds were serially diluted in neat DMSO and then diluted 1:100 v/v into media without FBS and mixed. Media was removed from the plated cells and the diluted compounds in serum free media (1% v/v final DMSO) were added and incubated at 37° C. for five hours. Ten uL of HDAC-Glo 2 reagent with 0.1% Triton X-100 was then added, the plate was mixed and allowed to develop at room temperature for 100 minutes. Plates were then read with a Spectramax LMax luminometer employing a 0.4 s integration time. Dose response curves were constructed with normalized data where CI-994 at 100 uM was defined as 100% inhibition and DMSO alone as 0% inhibition.

The results of this assay for certain compounds are reported in Table 3, below. In the table, "A" indicates an $IC_{50}$ value of between 0.1 µM and 1 µM; "B" indicates an a $IC_{50}$ value of between 1.0 µM and 1.5 µM; and "C" indicates an a $IC_{50}$ value of greater than 1.5 µM.

TABLE 3

| Compound No. | HDAC2 IC50, SH-SY5Y Cell Lysate (uM) |
| --- | --- |
| 1 | A |
| 2 | B |
| 3 | A |
| 4 | B |
| 5 | B |
| 6 | C |
| 7 | A |
| 8 | A |
| 9 | A |
| 10 | A |

Erythroid and Myeloid CFU Assay

Clonogenic progenitors of human erythroid (CFU-E, BFU-E), granulocyte-monocyte (CFU-GM) and multipotential (CFU-GEMM) lineages were assessed in a semi-solid methylcellulose-based media formulation containing rhIL-3 (10 ng/mL), rhGM-SCF (10 ng/mL), rhSCF (50 ng/mL) and Epo (3 U/mL).

Cells

Normal human bone marrow light density cells derived from normal bone marrow (NorCal Biologics, California) and qualified at ReachBio, were stored in the gaseous phase of liquid nitrogen (−152° C.) until required for the assay. On the day of the experiment, the cells were thawed rapidly, the contents of each vial was diluted in 10 mL of Iscove's modified Dulbecco's medium containing 10% fetal bovine serum (IMDM+10% FBS) and washed by centrifugation (approximately 1200 r.p.m. for 10 minutes, room temperature). The supernatant was discarded and the cell pellets resuspended in a known volume of EIDM+10% FBS. A cell count (3% glacial acetic acid) and viability assessment (trypan blue exclusion test) was performed for the bone marrow sample.

Compounds

On the day of the experiment, the compounds were dissolved in DMSO to a stock concentration of 10 mM. Serial dilutions were prepared from the stock concentration to achieve concentrations of 2 and 0.4 mM. When added to the methylcellulose-based media at 1:1000 (v/v), the final test concentrations of 10, 2 and 0.4 µM were achieved. Additionally, 5-FU was evaluated at 1.0, 0.1 and 0.01 µg/mL.

Method Summary

Clonogenic progenitors of the human erythroid (CFU-E and BFU-E) and myeloid (CFU-GM) lineages were set up in the methylcellulose-based media formulations described above. All compounds were added to the medium to give the final desired concentrations (10, 2 and 0.4 µM). 5-Fluorouracil (Sigma Aldrich) was used as a positive control for progenitor proliferation (inhibition of colony growth) and was introduced to the human bone marrow cultures at 1.0, 0.1, and 0.01 µg/mL. Solvent control cultures (containing no compound but 0.1% DMSO) as well as standard controls (containing no compound and no DMSO) were also initiated.

Human myeloid and erythroid progenitor assays were initiated at $2.0 \times 10^4$ cells per culture. Following 14 days in culture, myeloid and erythroid colonies were assessed microscopically and scored by trained personnel. The colonies were divided into the following categories based on size and morphology: CFU-E, BFU-E, CFU-GM and CFU-GEMM.

Statistical Analyses of CFC Numbers

The mean ± one standard deviation of three replicate cultures was calculated for progenitors of each category (CFU-E, BFU-E, etc.). Two-tailed t-tests were performed to assess if there was a difference in the number of colonies generated between solvent control and treated cultures. Due to the potential subjectivity of colony enumeration, a p value of less than 0.01 is deemed significant. To calculate the concentration of 50% inhibition of colony growth ($IC_{50}$) for each compound, a dose response curve was generated plotting the log of the compound concentration versus the percentage of control colony growth using XLfit software (IDBS). The concentration of 50% inhibition of colony growth ($IC_{50}$) was calculated based on the sigmoid curve fit using Dose-Response, One-Site Model formula: $y=A+[(B-A)/(1+((C/x)^D))]$, where A=the initial value (baseline response), B=maximum response, C=center (drug concentration that provokes a response halfway between A and B) and D=slope of the curve at midpoint. Further, plots and additional dose response curves were generated using GraphPad Prism 7.0.

Morphological Assessment of Colonies

Photographs were taken of representative hematopoietic progenitor-derived colonies from various lineages, illustrating colonies in the presence of the solvent control as well as colonies in the presence of the test compounds.

Erythroid (CFU-E and BFU-E), myeloid (CFU-GM) and multi-potential (CFU-GEMM) colony enumeration was performed by trained personnel. The distribution of colony types as well as general colony and cellular morphology was analyzed. For statistical analysis colony numbers in compound treated cultures were compared to the solvent control cultures. 5-FU was used as a positive control for toxicity in these assays and the inhibitory effects obtained for this compound were exactly as expected. The experiment was used to evaluate the potential effect of test compounds on human erythroid and myeloid progenitor proliferation in a methylcellulose-based medium. The $IC_{50}$ values were calculated from XLfit. Dose response curves for erythroid and myeloid toxicity generated by XLfit. Finally, nonlinear regression curve fitting and $IC_{50}s \pm 9500$ CI, were calculated by Prism 7.0.-GEMM.

Results are shown in Table 4.

TABLE 4

| Compound | Structure | Erythroid % control remaining @ 10 uM dose | Myeloid % control remaining @ 10 uM dose |
|---|---|---|---|
| Comparator 1 | 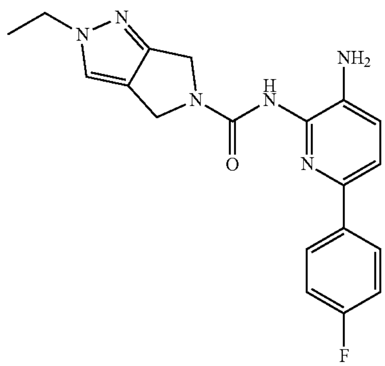 [SMILES: CCn1cc2c(n1)CN(C(=O)Nc1nc(-c3ccc(F)cc3)ccc1N)C2] | 22 | 34 |
| 10 | 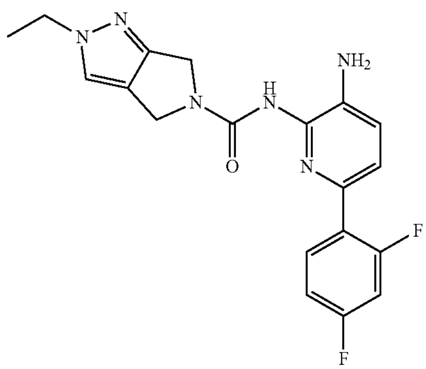 [SMILES: CCn1cc2c(n1)CN(C(=O)Nc1nc(-c3ccc(F)cc3F)ccc1N)C2] | 38 | 77 |
| Comparator 2 | 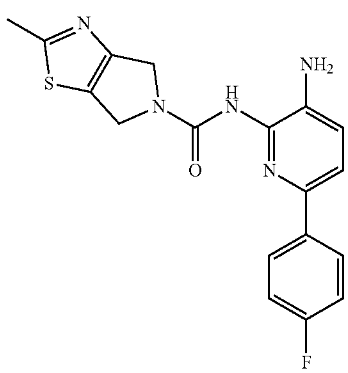 [SMILES: Cc1nc2c(s1)CN(C(=O)Nc1nc(-c3ccc(F)cc3)ccc1N)C2] | 45 | 103 |
| 3 | 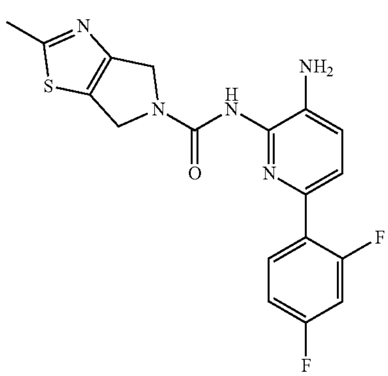 [SMILES: Cc1nc2c(s1)CN(C(=O)Nc1nc(-c3ccc(F)cc3F)ccc1N)C2] | 89 | 109 |

TABLE 4-continued

| Compound | Structure | Erythroid % control remaining @ 10 uM dose | Myeloid % control remaining @ 10 uM dose |
| --- | --- | --- | --- |
| Comparator 3 | 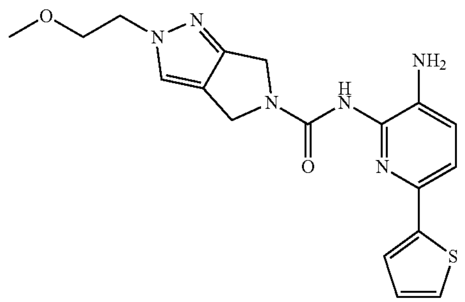 [SMILES: COCCn1cc2c(n1)CN(C(=O)Nc1nc(-c3cccs3)ccc1N)C2] | 18 | 9 |
| 6 | 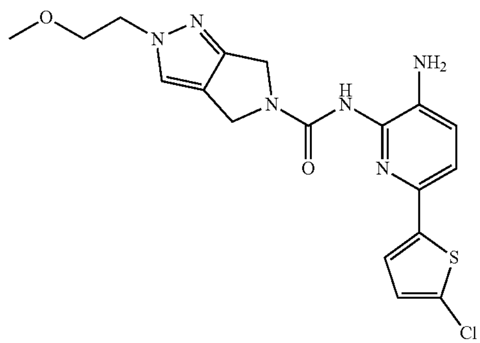 [SMILES: COCCn1cc2c(n1)CN(C(=O)Nc1nc(-c3ccc(Cl)s3)ccc1N)C2] | 69 | 82 |
| Comparator 4 | 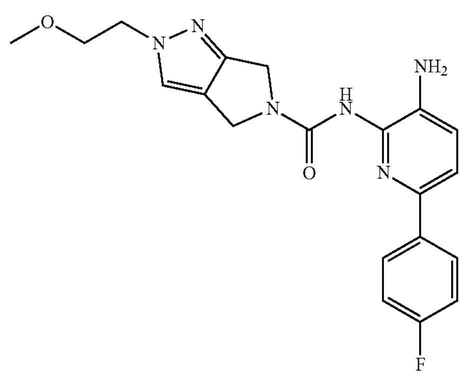 [SMILES: COCCn1cc2c(n1)CN(C(=O)Nc1nc(-c3ccc(F)cc3)ccc1N)C2] | 28 | 39 |
| 8 | 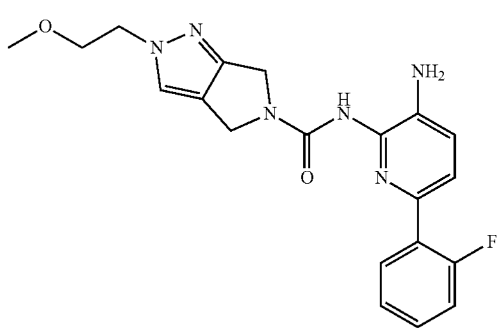 [SMILES: COCCn1cc2c(n1)CN(C(=O)Nc1nc(-c3ccccc3F)ccc1N)C2] | 72 | 75 |

TABLE 4-continued

| Compound | Structure | Erythroid % control remaining @ 10 uM dose | Myeloid % control remaining @ 10 uM dose |
| --- | --- | --- | --- |
| Comparator 5 | 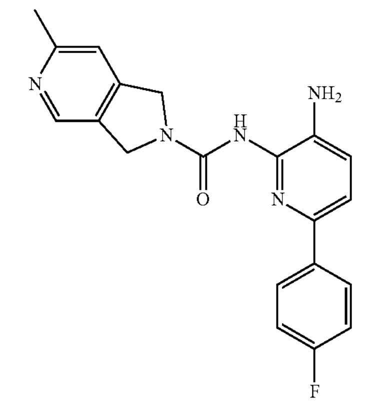 [SMILES: Cc1cc2c(cn1)CN(C(=O)Nc1nc(-c3ccc(F)cc3)ccc1N)C2] | 25.7 | 66.1 |
| 1 | 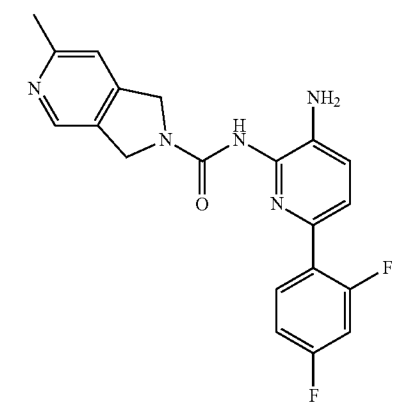 [SMILES: Cc1cc2c(cn1)CN(C(=O)Nc1nc(-c3ccc(F)cc3F)ccc1N)C2] | 53 | 100 |
| 5 | 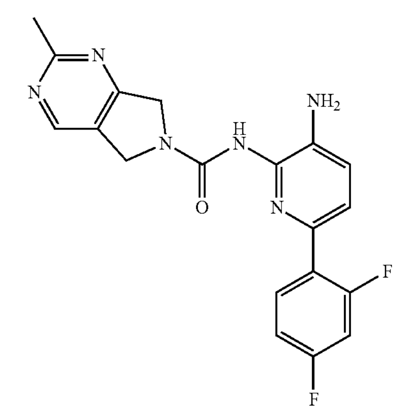 [SMILES: Cc1ncc2c(n1)CN(C(=O)Nc1nc(-c3ccc(F)cc3F)ccc1N)C2] | 69 | 82 |

TABLE 4-continued
| Compound | Structure | Erythroid % control remaining @ 10 uM dose | Myeloid % control remaining @ 10 uM dose |
|---|---|---|---|
| Comparator 6 | 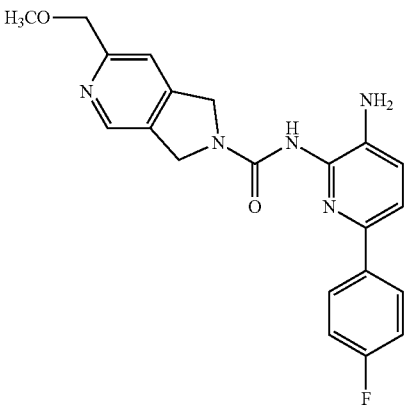 [SMILES: COCc1cc2c(cn1)CN(C(=O)Nc1nc(-c3ccc(F)cc3)ccc1N)C2] | 22.9 | 58.9 |
| 9 | 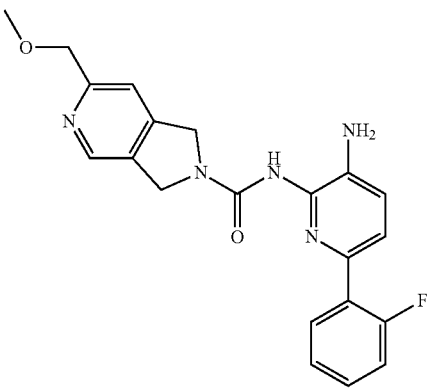 [SMILES: COCc1cc2c(cn1)CN(C(=O)Nc1nc(-c3ccccc3F)ccc1N)C2] | 87 | 102 |
| Comparator 7 | 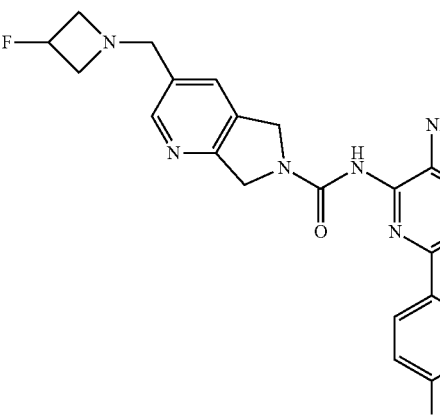 | 35 | 82 |

TABLE 4-continued
| Compound | Structure | Erythroid % control remaining @ 10 uM dose | Myeloid % control remaining @ 10 uM dose |
|---|---|---|---|
| 4 | 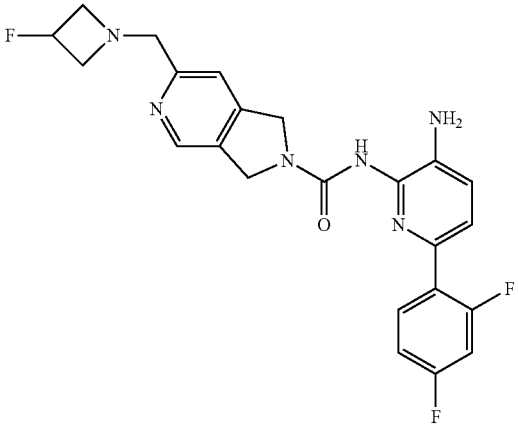 [SMILES: Nc1ccc(-c2ccc(F)cc2F)nc1NC(=O)N1Cc2cnc(CN3CC(F)C3)cc2C1] | 62 | 102 |
| Comparator 8 | 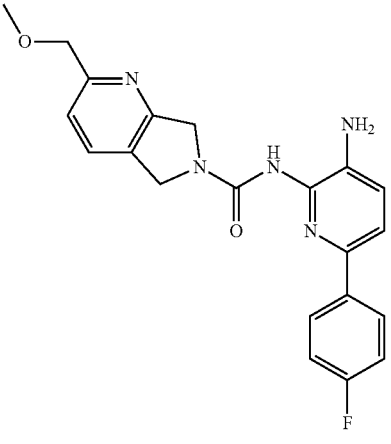 [SMILES: COCc1ccc2c(n1)CN(C(=O)Nc1nc(-c3ccc(F)cc3)ccc1N)C2] | 33 | 70 |
| 2 | 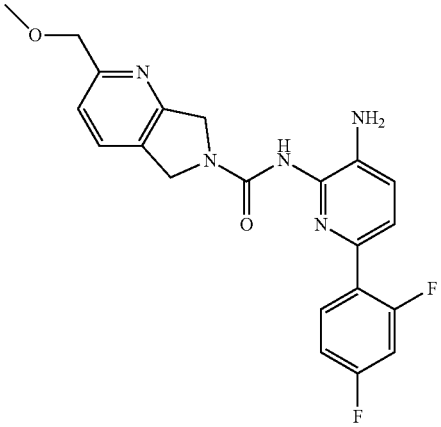 [SMILES: COCc1ccc2c(n1)CN(C(=O)Nc1nc(-c3ccc(F)cc3F)ccc1N)C2] | 62 | 92 |

TABLE 4-continued

| Compound | Structure | Erythroid % control remaining @ 10 uM dose | Myeloid % control remaining @ 10 uM dose |
|---|---|---|---|
| Comparator 9 | 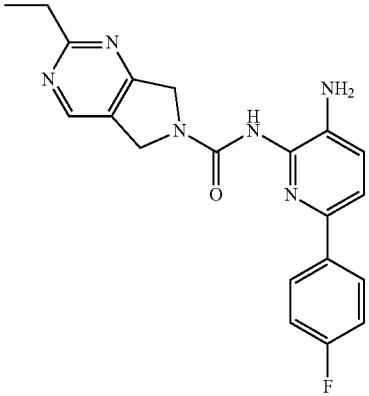 [SMILES: CCc1ncc2c(n1)CN(C(=O)Nc1nc(-c3ccc(F)cc3)ccc1N)C2] | 60 | 79 |
| 7 | 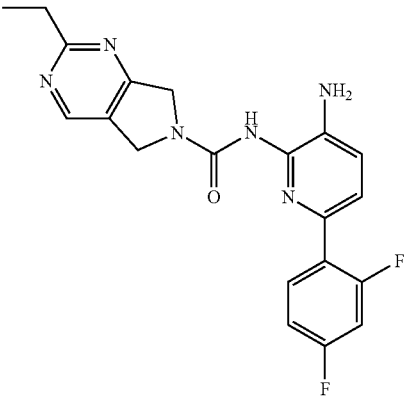 [SMILES: CCc1ncc2c(n1)CN(C(=O)Nc1nc(-c3ccc(F)cc3F)ccc1N)C2] | 69 | 105 |

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method for treating a cognitive function disorder, a cognitive function impairment, or a psychiatric disorder in a subject in need thereof, wherein the method comprises administering to the subject a therapeutically effective amount of a compound selected from the group consisting of:

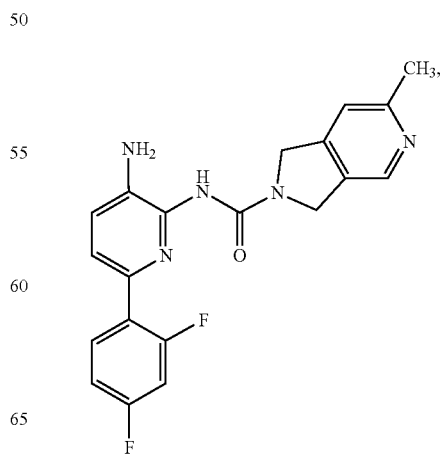

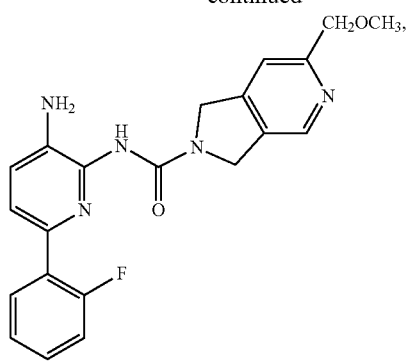
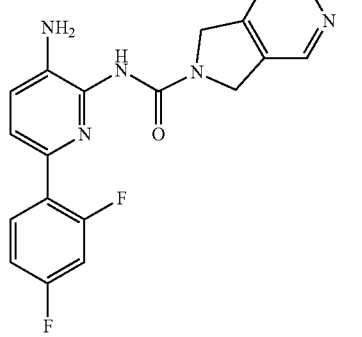
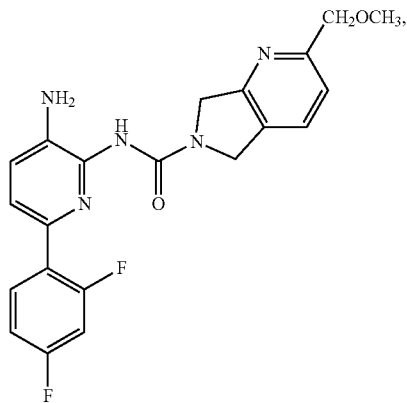
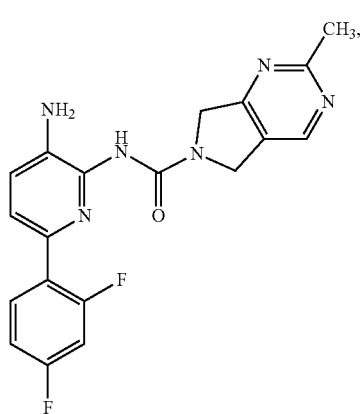
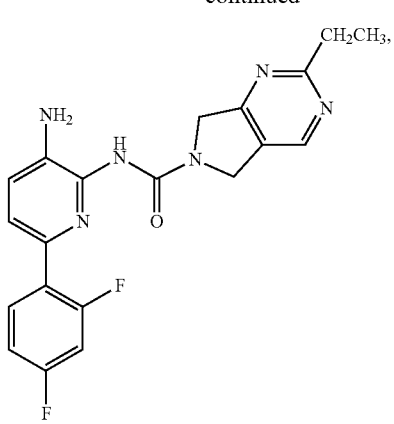
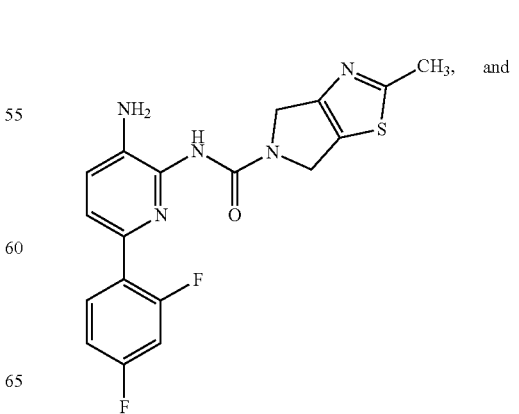

-continued

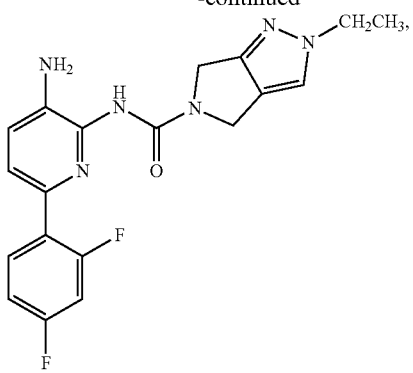

or a pharmaceutically acceptable salt of any of the foregoing.

2. The method of claim 1, wherein the compound is:

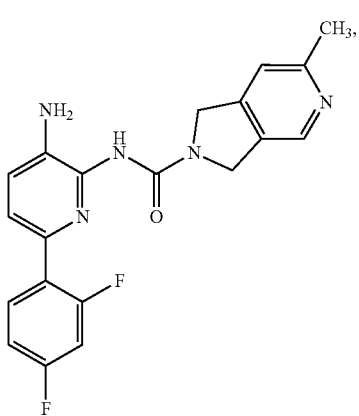 [SMILES: Cc1cc2c(cn1)CN(C(=O)Nc1nc(-c3ccc(F)cc3F)ccc1N)C2]

or a pharmaceutically acceptable salt thereof.

3. The method of claim 1, wherein the compound is:

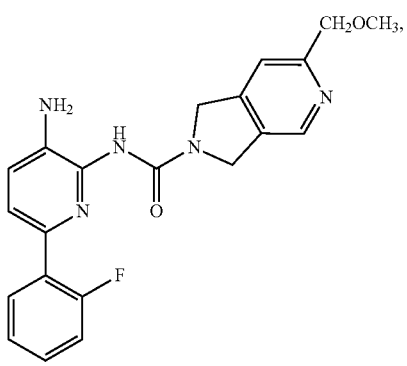

or a pharmaceutically acceptable salt thereof.

4. The method of claim 1, wherein the compound is:

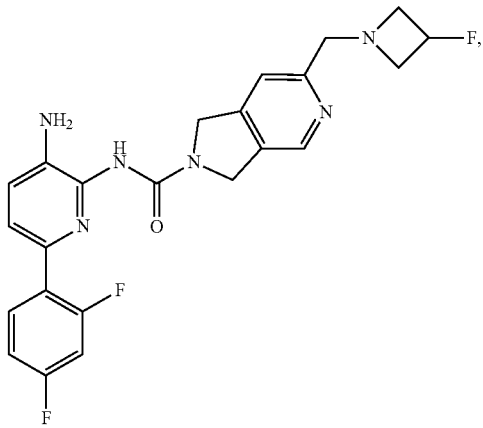 [SMILES: Nc1ccc(-c2ccc(F)cc2F)nc1NC(=O)N1Cc2cnc(CN3CC(F)C3)cc2C1]

or a pharmaceutically acceptable salt thereof.

5. The method of claim 1, wherein the compound is:

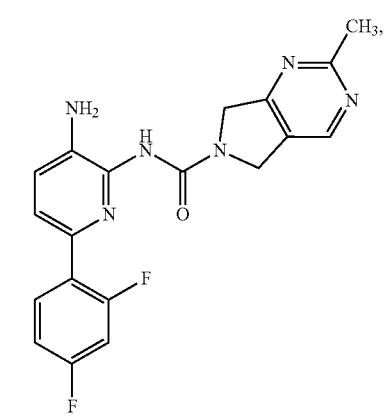 [SMILES: Cc1ncc2c(n1)CN(C(=O)Nc1nc(-c3ccc(F)cc3F)ccc1N)C2]

or a pharmaceutically acceptable salt thereof.

6. The method of claim 1, wherein the compound is:

or a pharmaceutically acceptable salt thereof.

7. The method of claim 1, wherein the compound is:

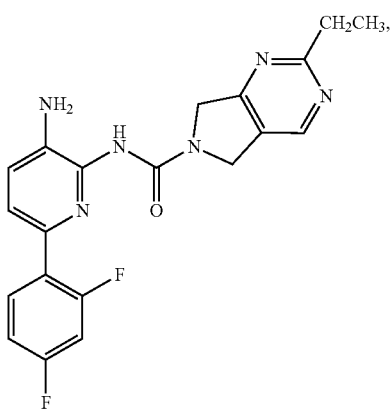 [SMILES: CCc1ncc2c(n1)CN(C(=O)Nc1nc(-c3ccc(F)cc3F)ccc1N)C2]

or a pharmaceutically acceptable salt thereof.

8. The method of claim 1, wherein the compound is:

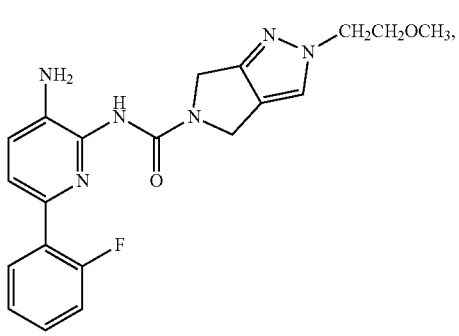

or a pharmaceutically acceptable salt thereof.

9. The method of claim 1, wherein the compound is:

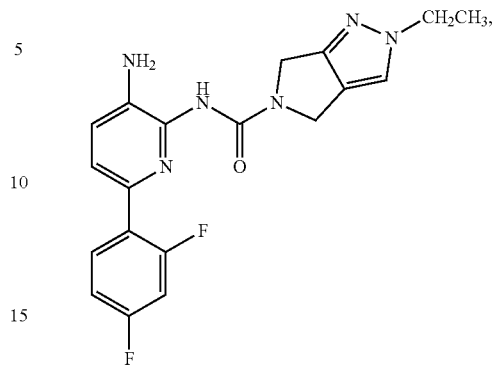

or a pharmaceutically acceptable salt thereof.

10. The method of claim 1, wherein the compound is:

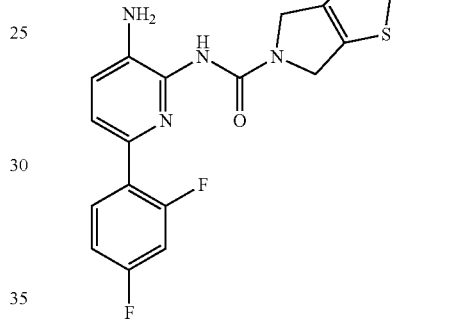

or a pharmaceutically acceptable salt thereof.

* * * * *